(12) United States Patent
Reis et al.

(10) Patent No.: US 8,720,448 B2
(45) Date of Patent: May 13, 2014

(54) STERILE INTERFACE APPARATUS

(75) Inventors: Gene Reis, San Jose, CA (US); Gregory J. Stahler, San Jose, CA (US); Gregory Francis Hirth, Pleasanton, CA (US); Enrique Romo, Dublin, CA (US)

(73) Assignee: Hansen Medical, Inc., Mountain View, CA (US)

( * ) Notice: Subject to any disclaimer, the term of this patent is extended or adjusted under 35 U.S.C. 154(b) by 1044 days.

(21) Appl. No.: 12/614,349

(22) Filed: Nov. 6, 2009

(65) Prior Publication Data
US 2010/0170519 A1 Jul. 8, 2010

Related U.S. Application Data

(60) Provisional application No. 61/112,570, filed on Nov. 7, 2008.

(51) Int. Cl.
*A61B 19/08* (2006.01)

(52) U.S. Cl.
USPC ............................ 128/852; 606/130; 600/121

(58) Field of Classification Search
USPC ............... 128/849–856; 606/1, 130; 600/121, 600/124–125; 901/49–50; 700/245
See application file for complete search history.

(56) References Cited

U.S. PATENT DOCUMENTS

| 4,736,660 | A | 4/1988 | Benach et al. |
|---|---|---|---|
| 6,824,511 | B1 | 11/2004 | Bell et al. |
| 2005/0222554 | A1 | 10/2005 | Wallace et al. |
| 2006/0084911 | A1* | 4/2006 | Belef et al. ................. 604/95.01 |
| 2006/0084945 | A1 | 4/2006 | Moll et al. |
| 2006/0095022 | A1 | 5/2006 | Moll et al. |
| 2007/0043338 | A1 | 2/2007 | Moll et al. |
| 2007/0239172 | A1* | 10/2007 | Lee et al. ...................... 606/130 |
| 2008/0140087 | A1 | 6/2008 | Barbagli |
| 2008/0234631 | A1 | 9/2008 | Reis |
| 2010/0175701 | A1 | 7/2010 | Reis et al. |

FOREIGN PATENT DOCUMENTS

WO    WO 2010/081050    7/2010

\* cited by examiner

*Primary Examiner* — Patricia Bianco
*Assistant Examiner* — Kari Petrik
(74) *Attorney, Agent, or Firm* — Rader, Fishman & Grauer PLLC

(57) ABSTRACT

A robotic surgical system configured to perform minimally invasive surgical procedures. In one variation, this robotic surgical system includes an instrument driver configured to steer an elongate instrument of an instrument assembly in one or more degrees of motion. A drape is disposed between the instrument driver and the instrument assembly. A drive interface apparatus is operatively coupled to the drape. The drape and drive interface apparatus may form a fluid barrier between the instrument driver and the instrument assembly. Drive interface apparatus may be disposed on a top surface of the instrument driver and on a bottom surface of the instrument assembly. The drive interface apparatus may transmit torque from the instrument driver to the instrument assembly. The input torque drives a pulley in the instrument assembly that operates one or more control wires to steer an elongate instrument of the instrument assembly for performing minimally invasive surgical procedures.

24 Claims, 35 Drawing Sheets

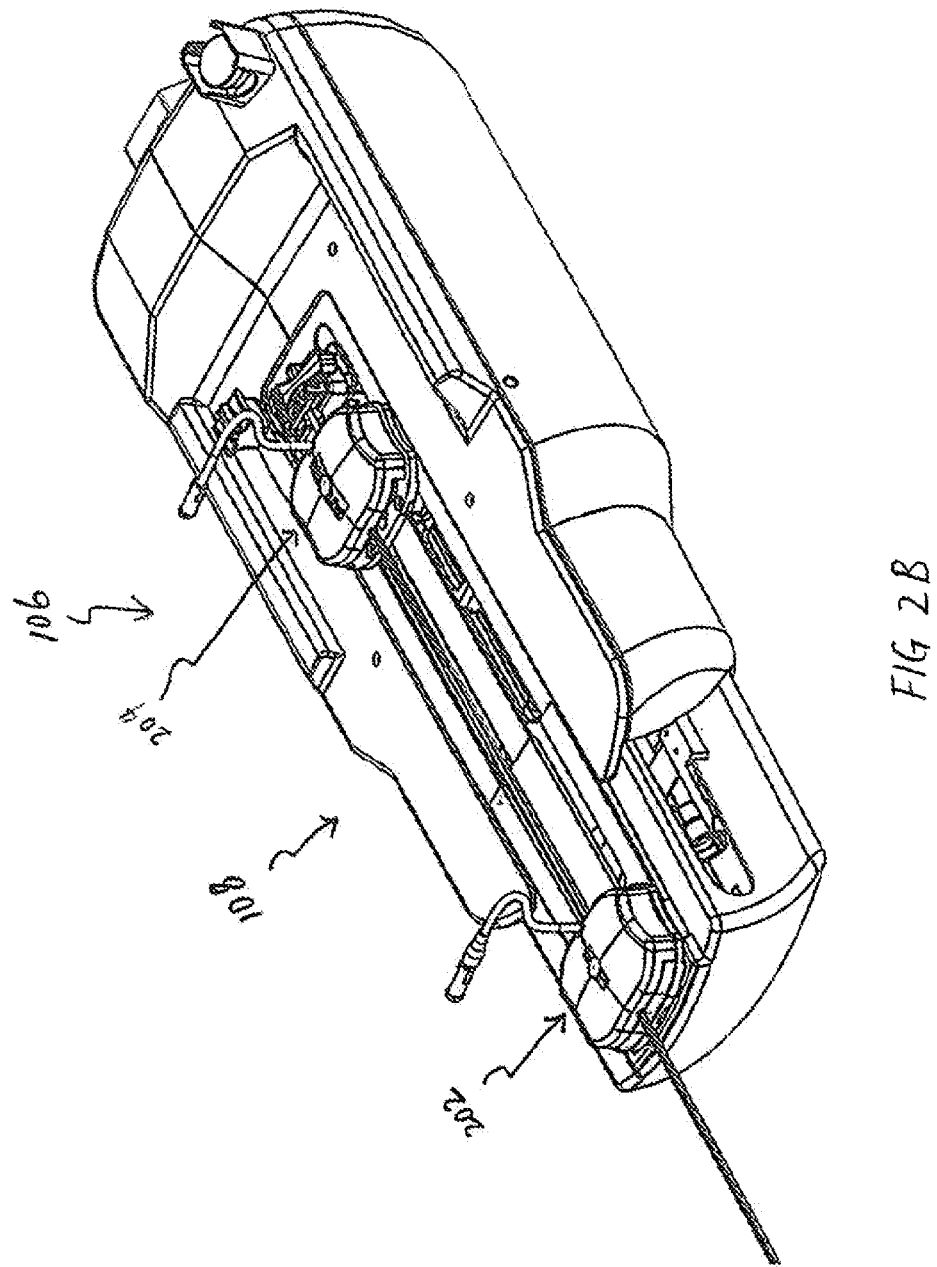

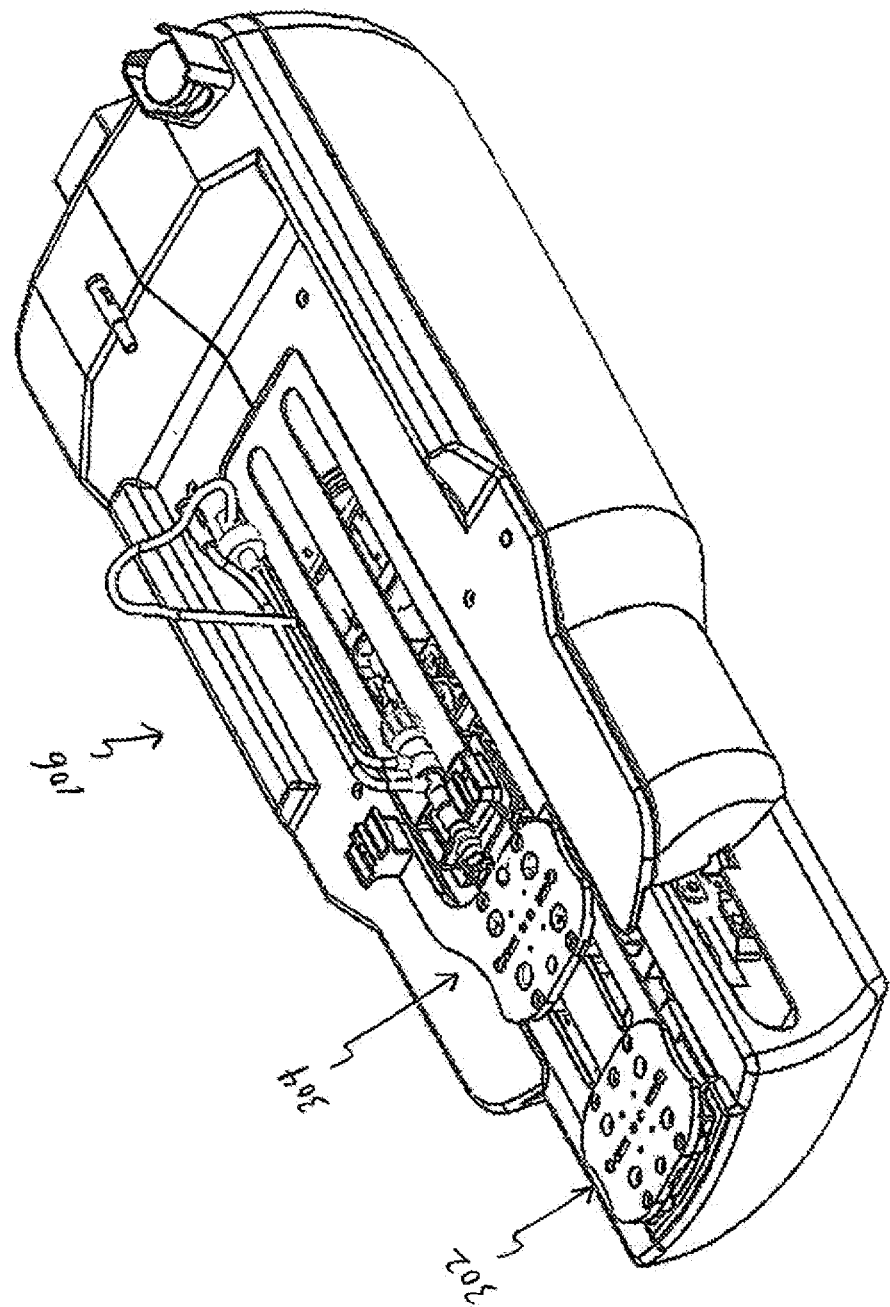

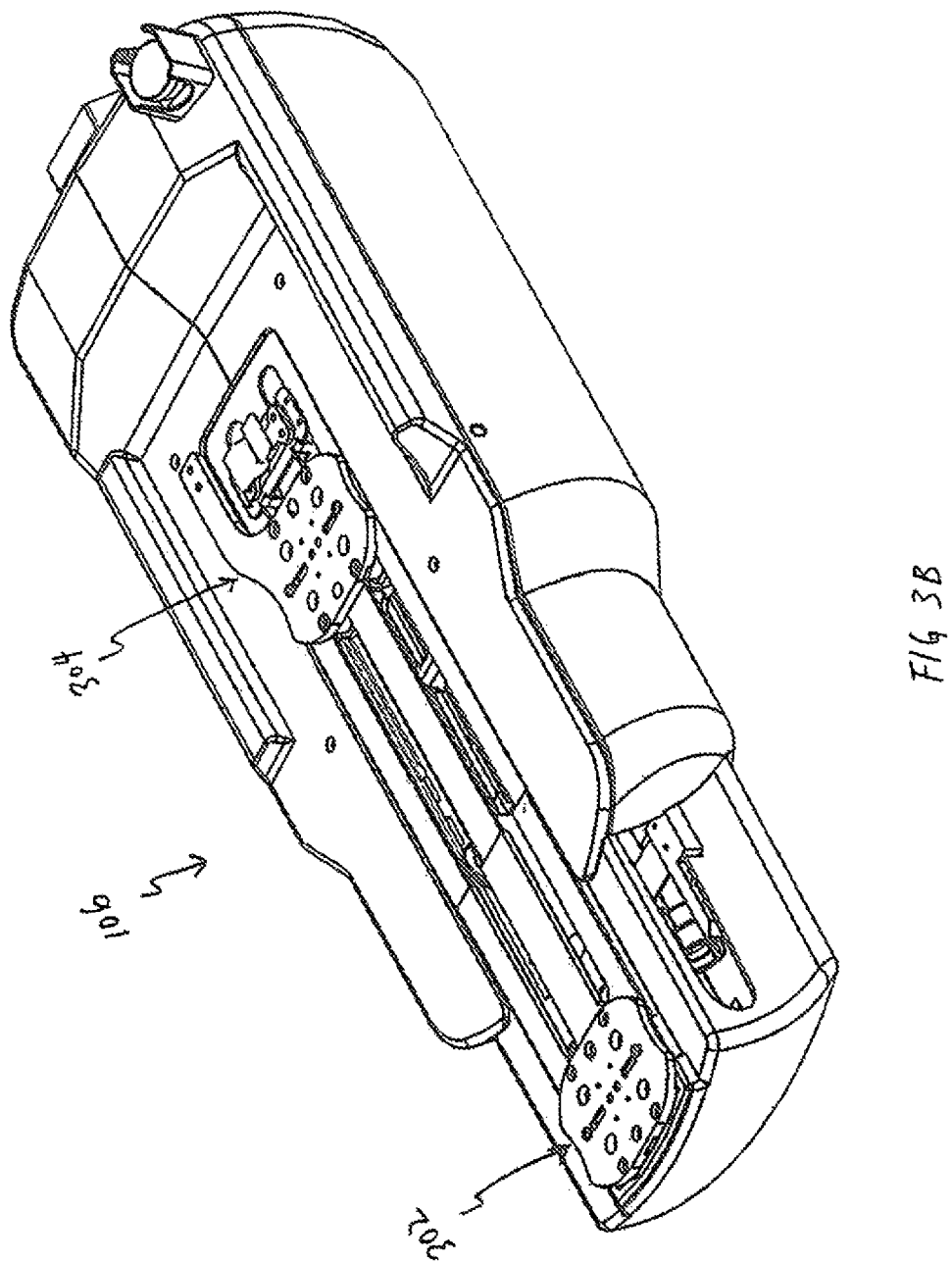

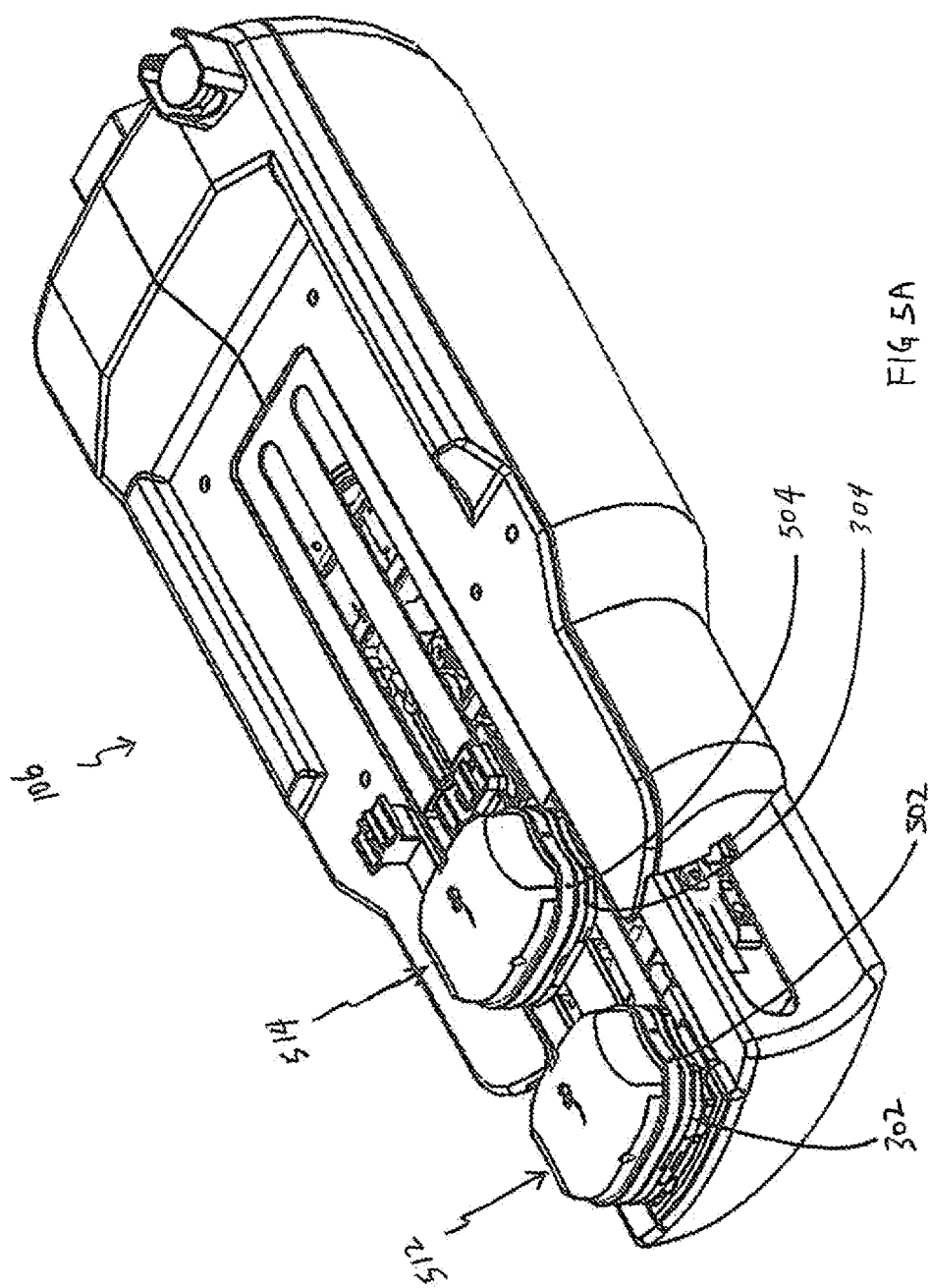

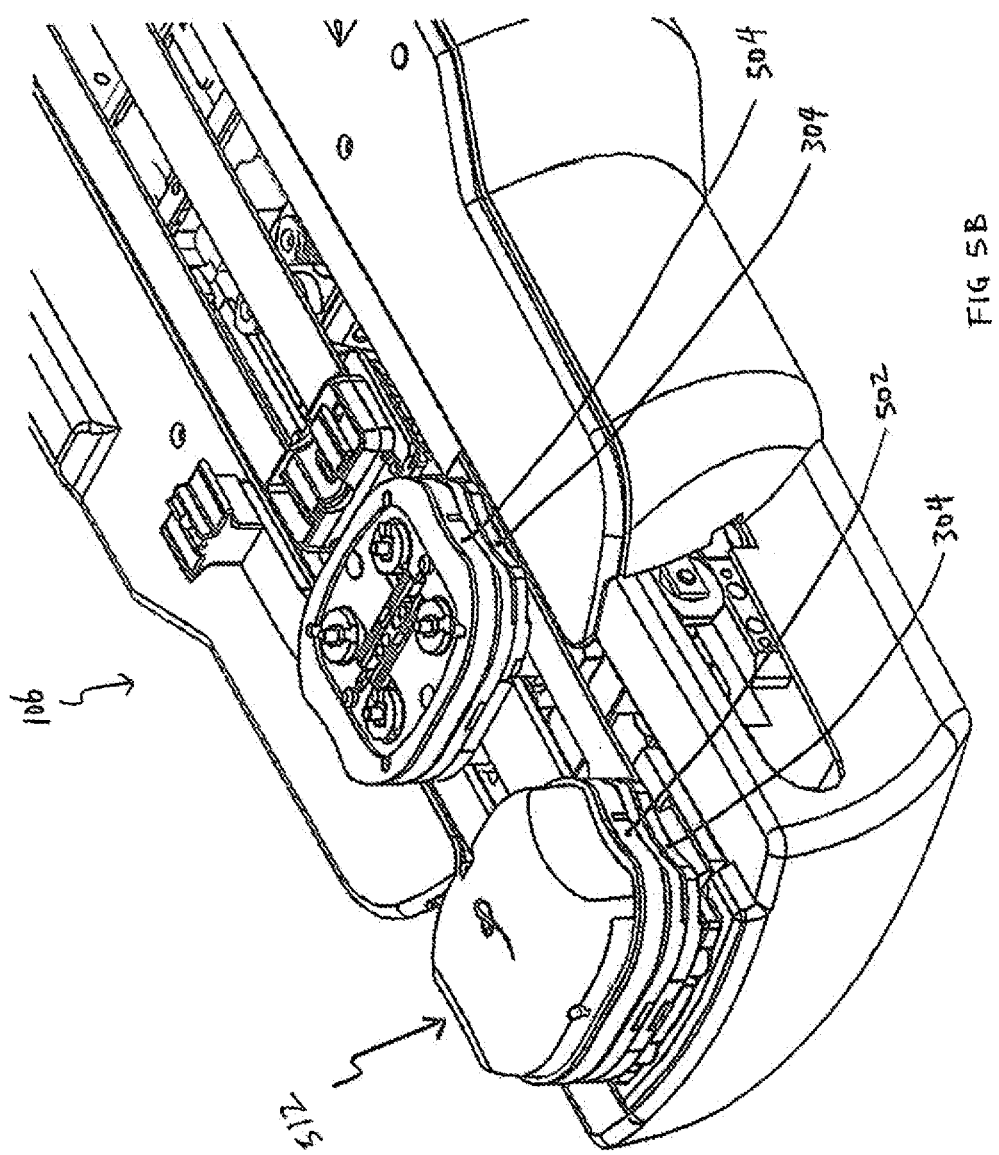

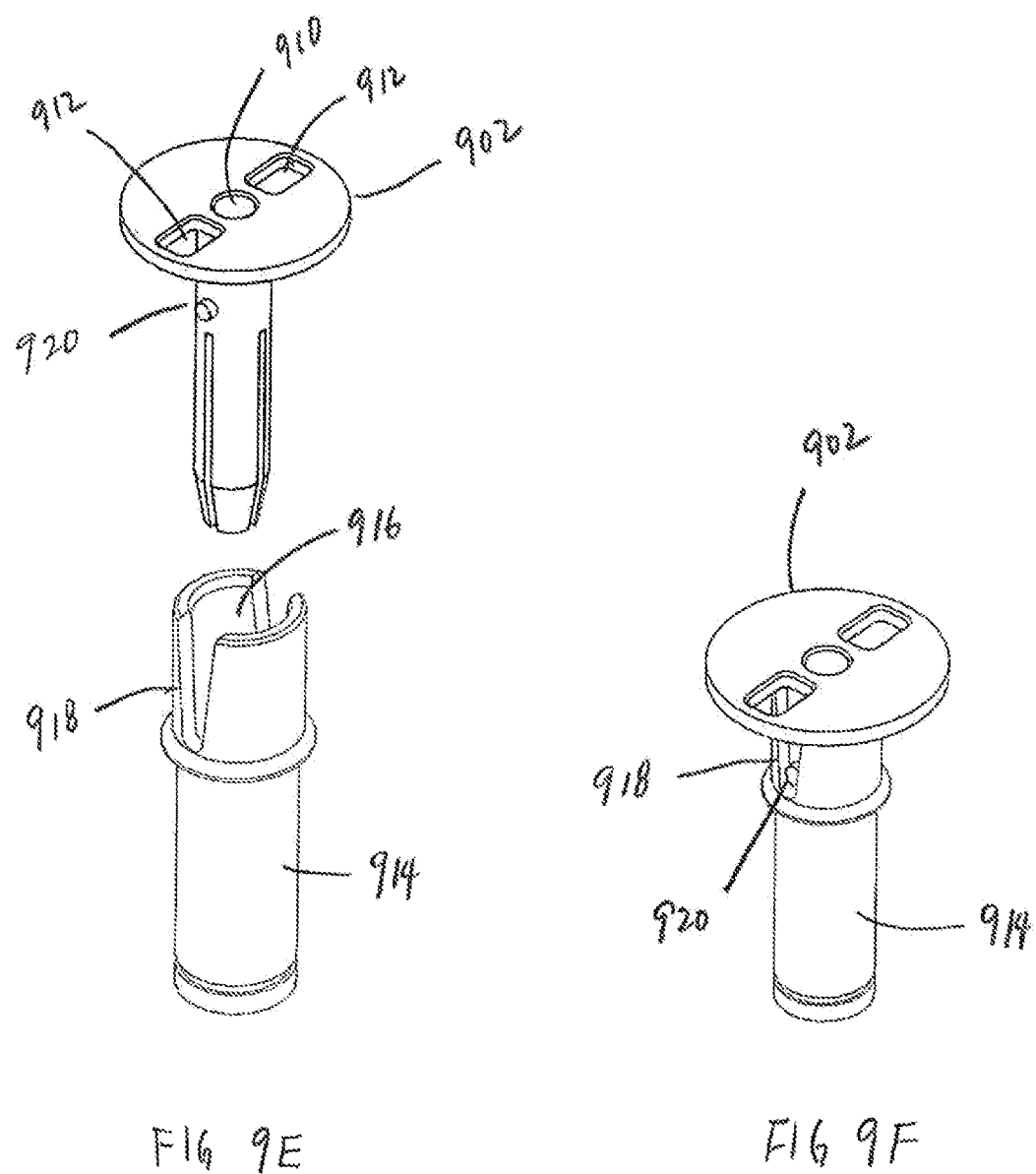

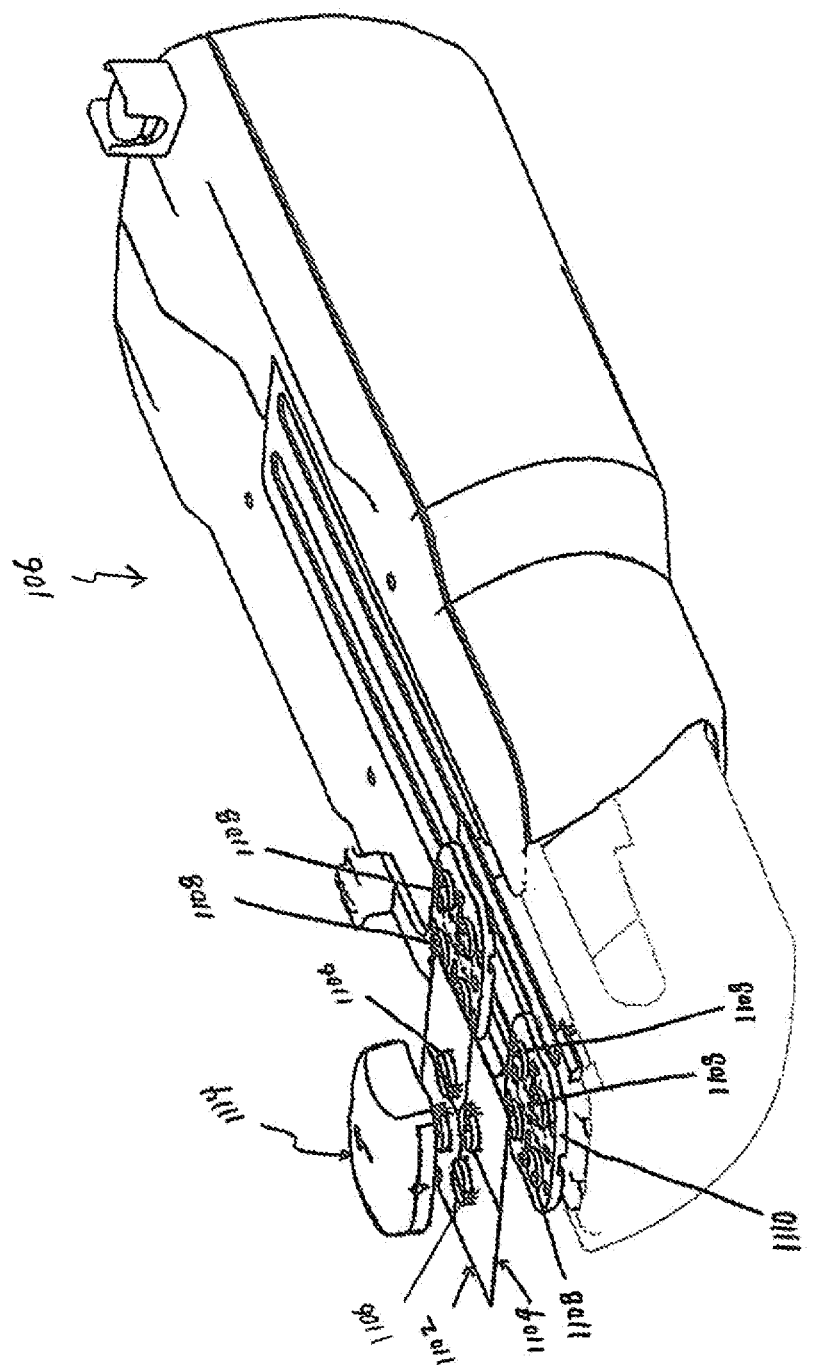

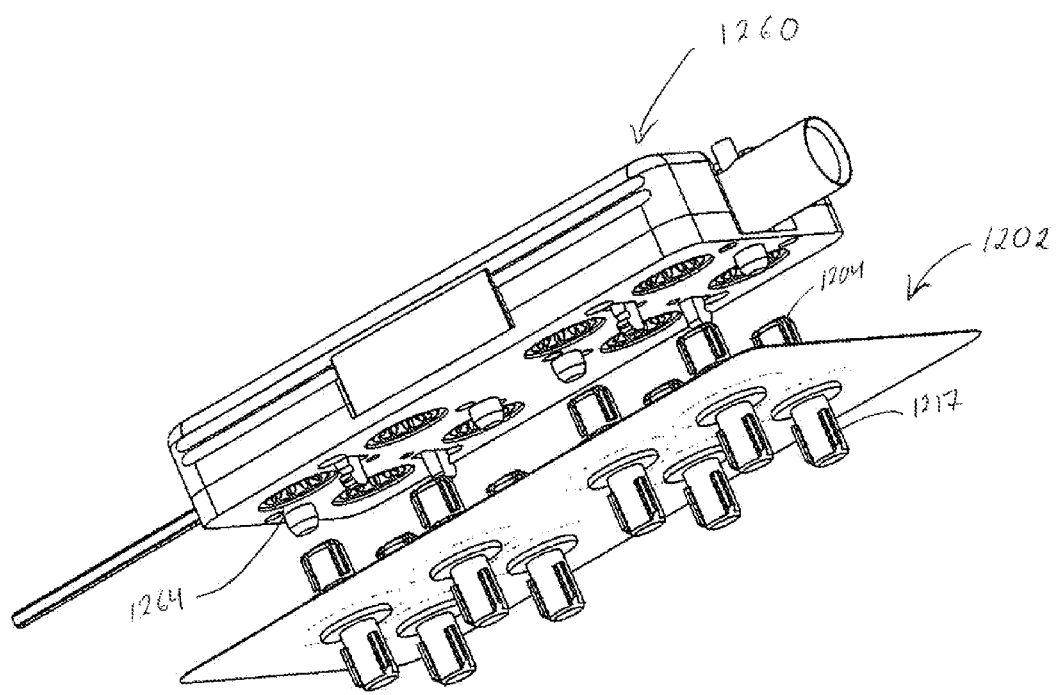

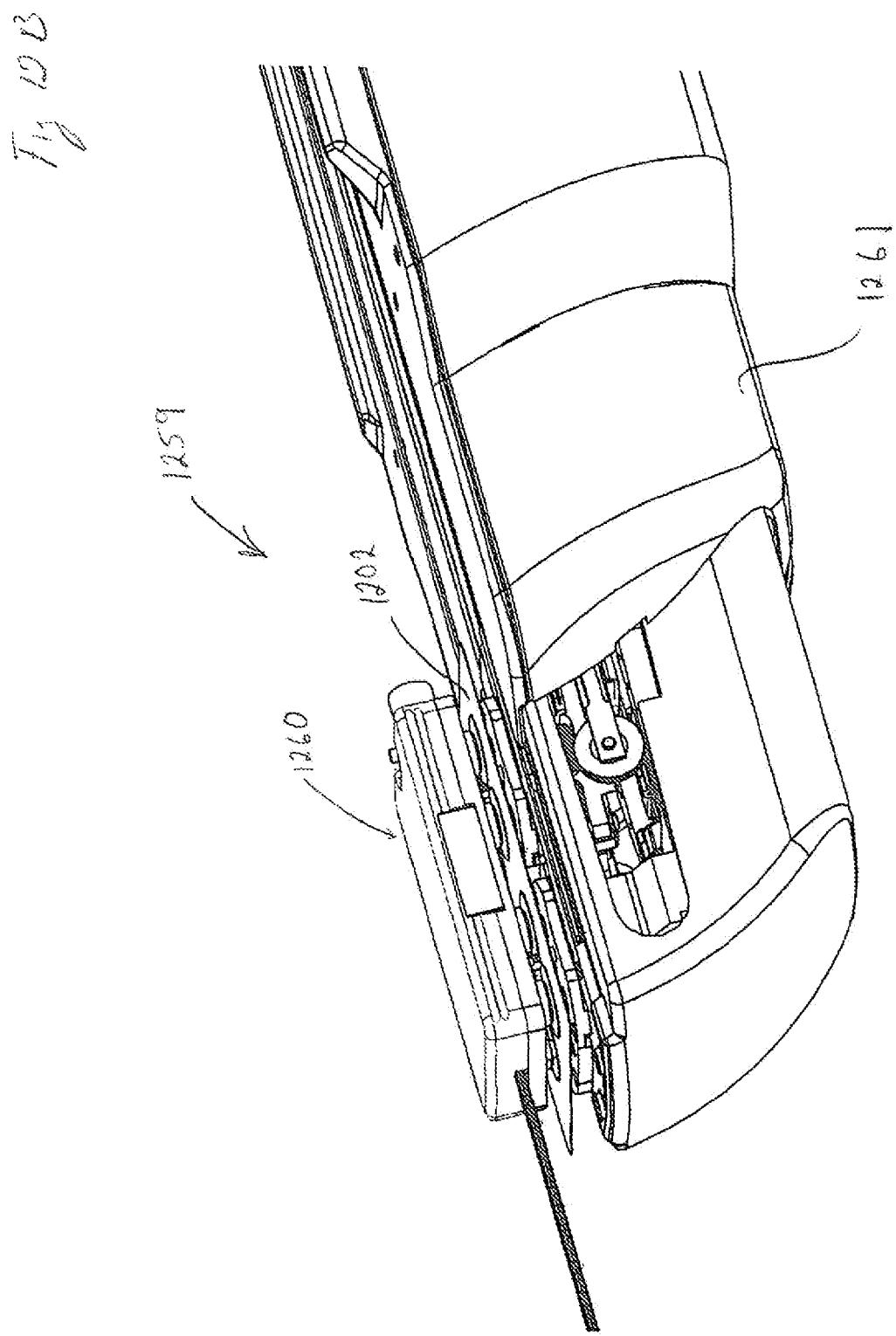

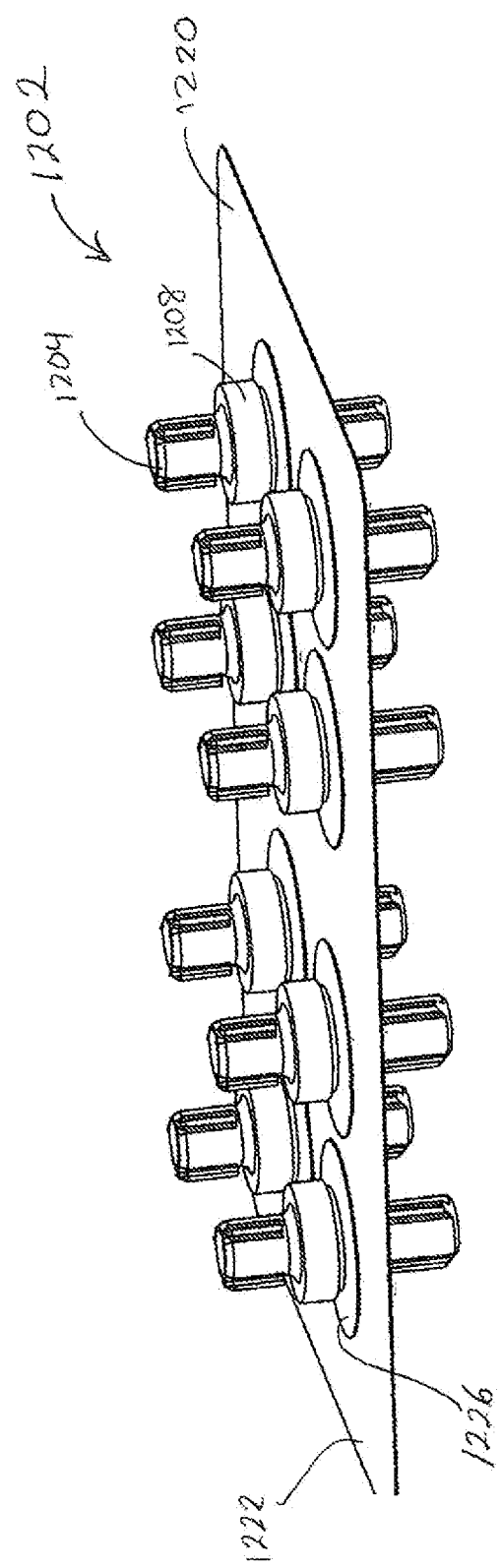

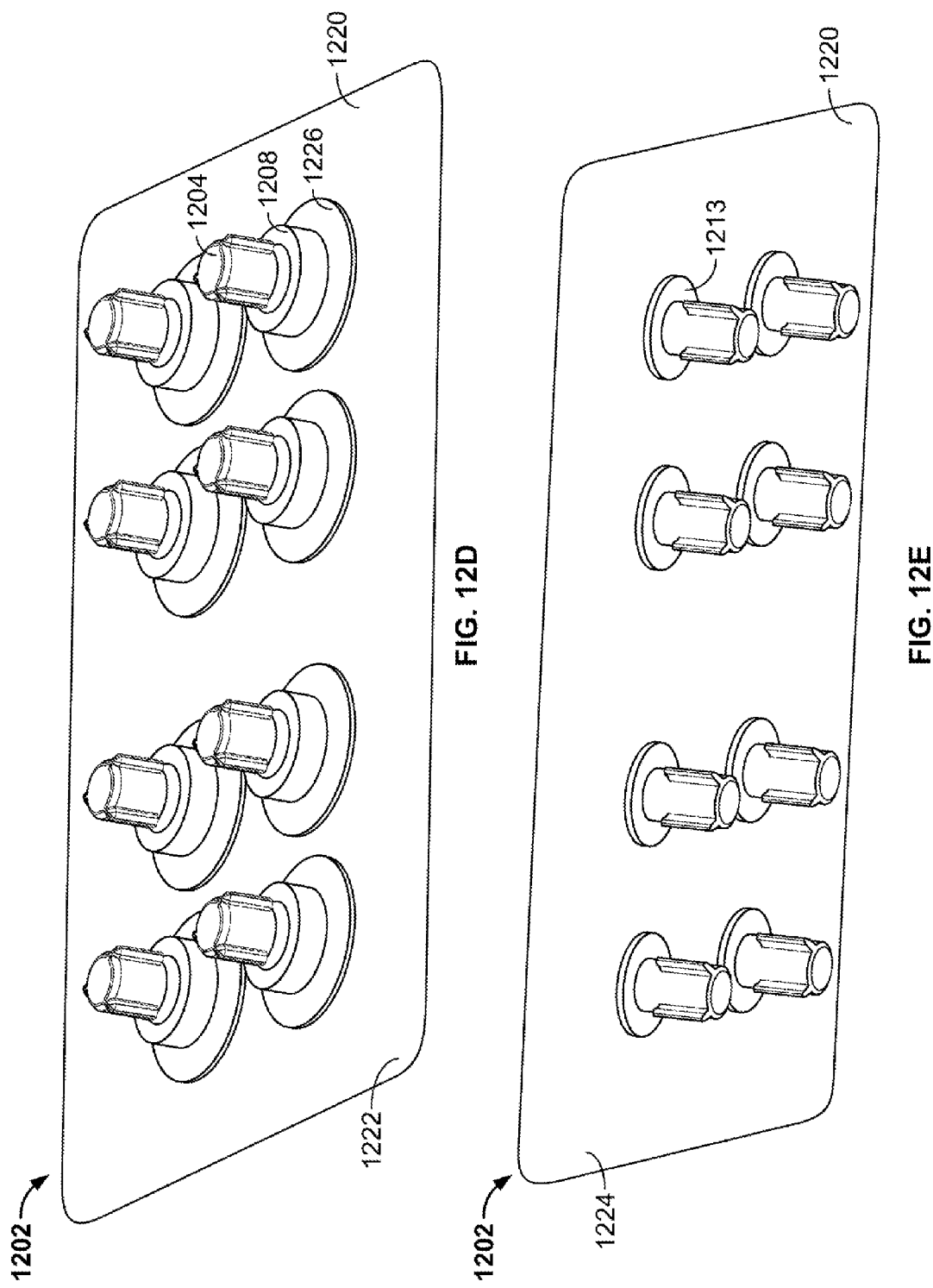

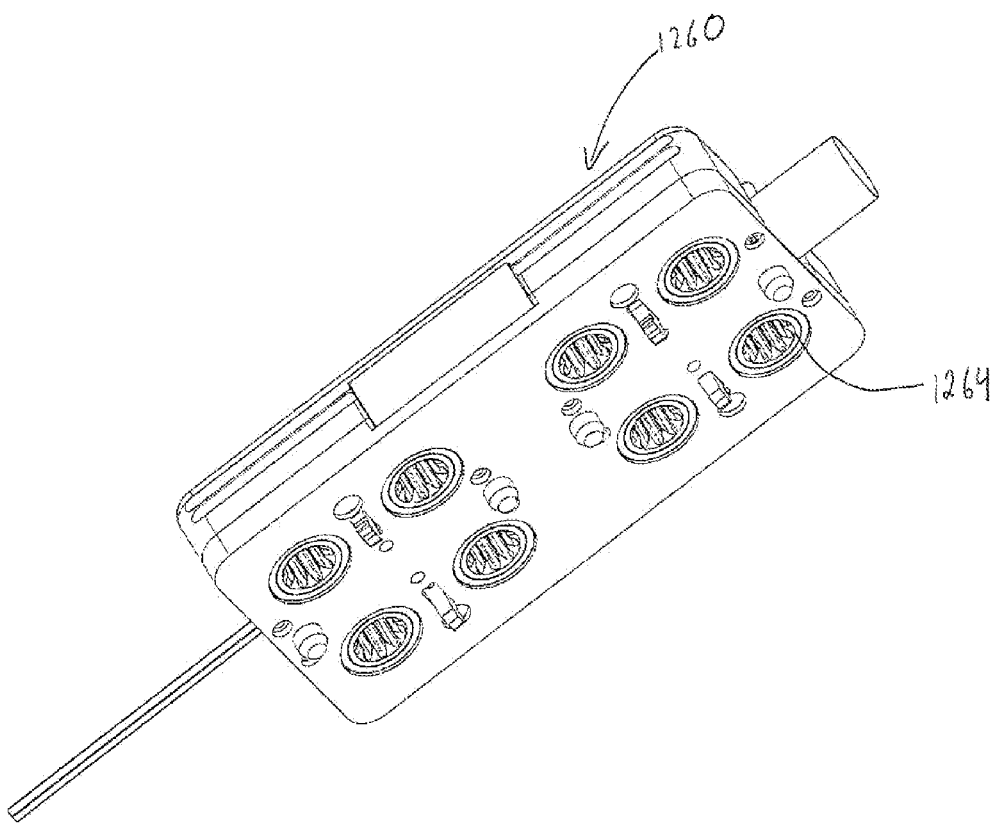

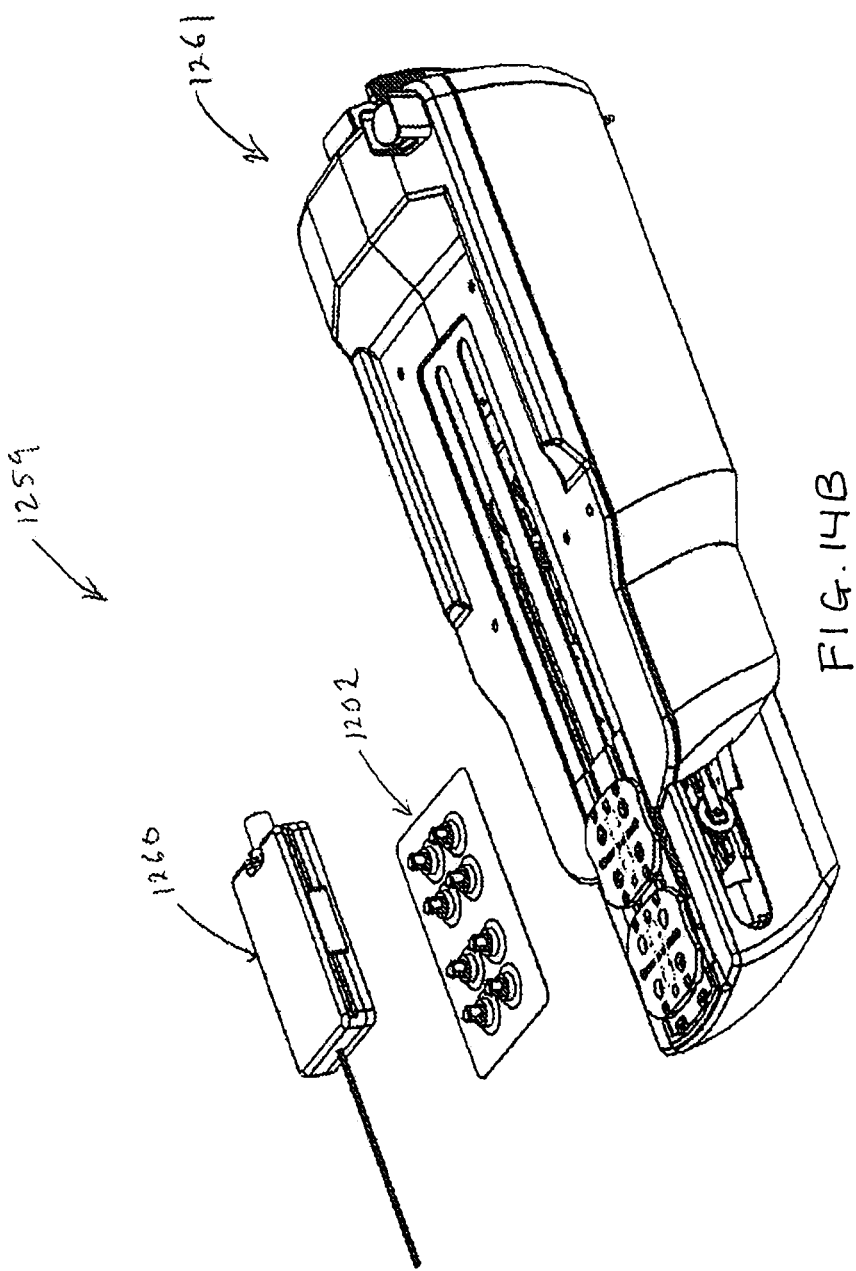

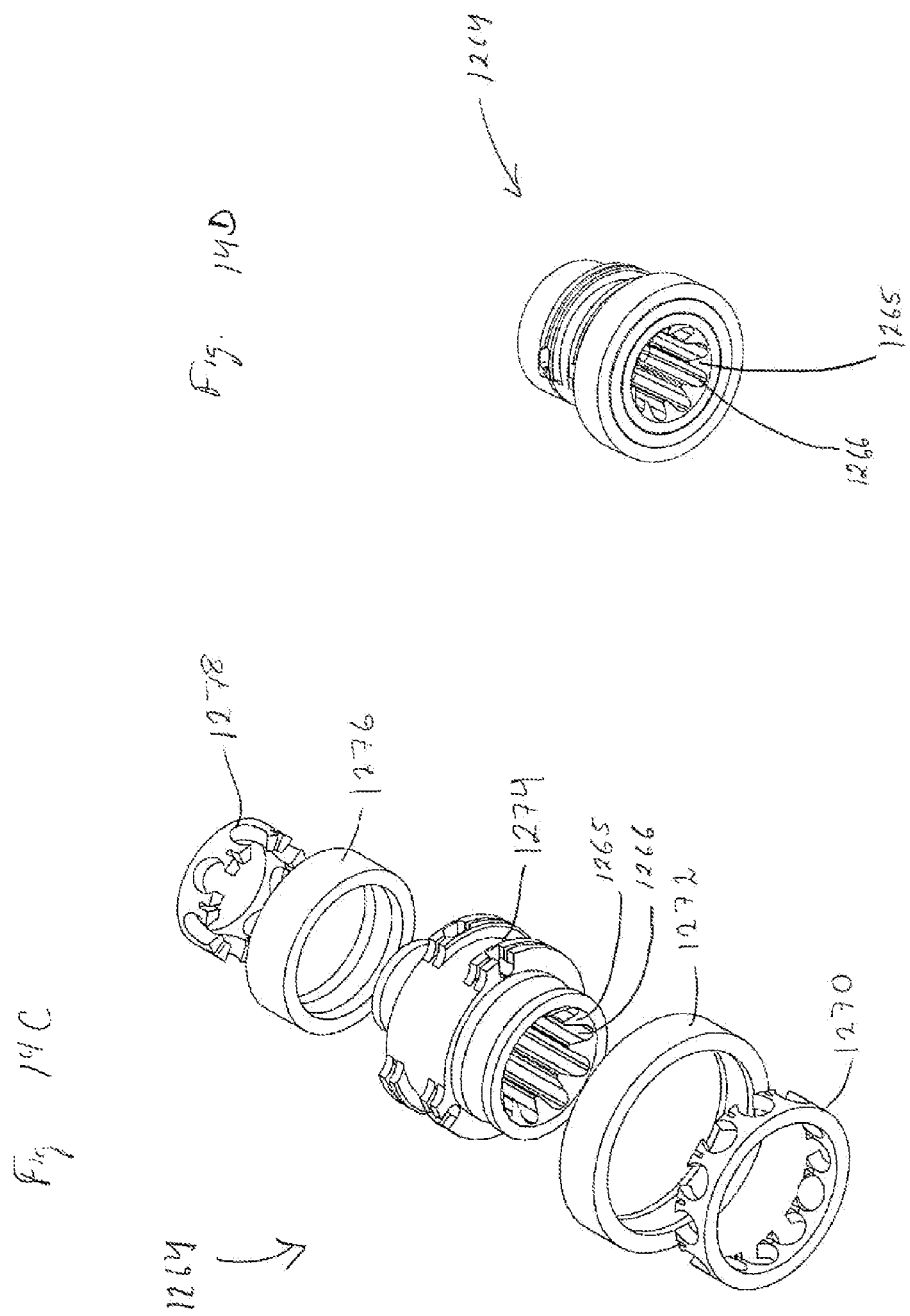

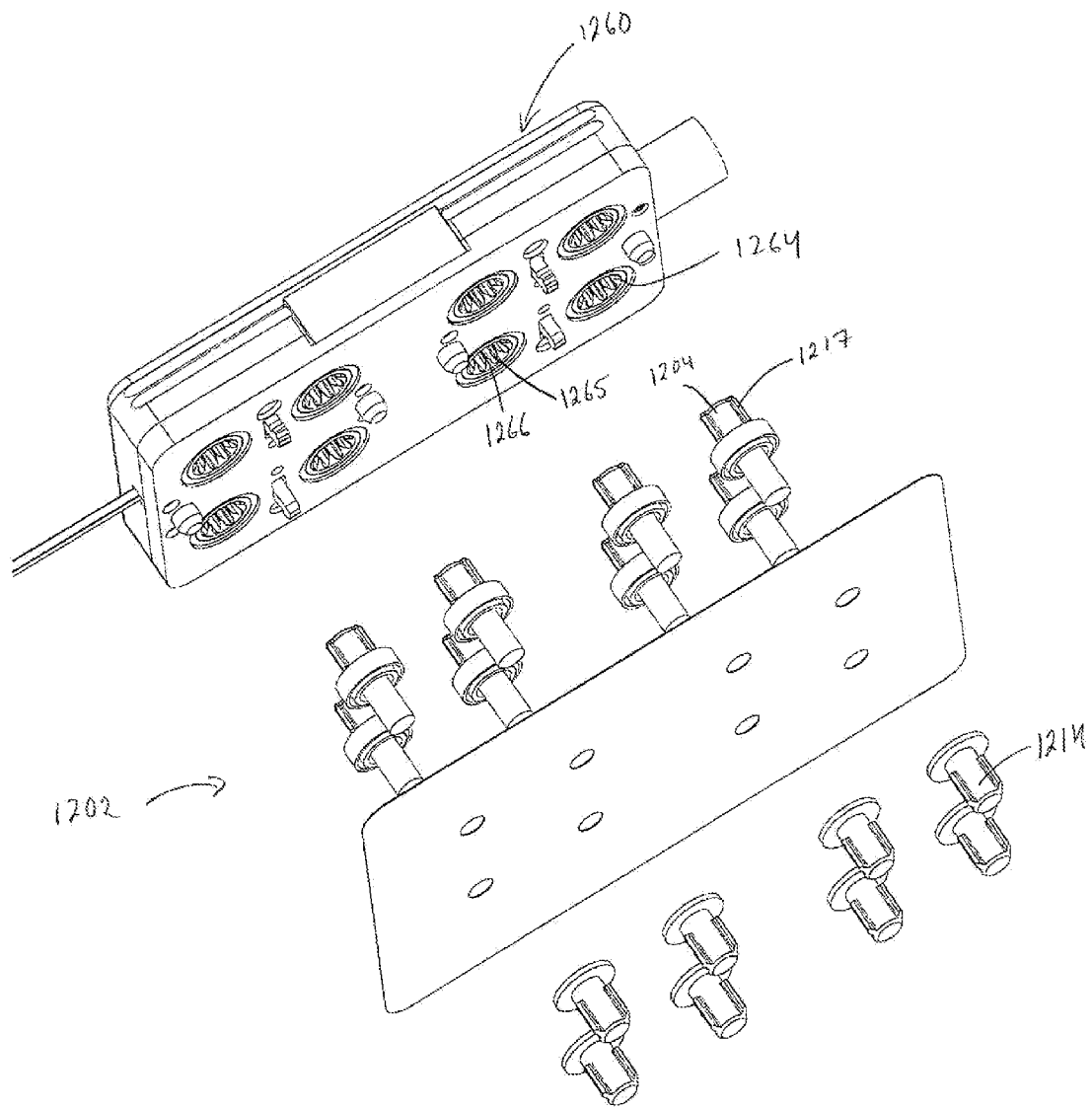

STERILE INTERFACE APPARATUS

CROSS-REFERENCE TO RELATED APPLICATION

This application claims the benefit of priority to U.S. Prov. Pat. App. 61/112,570 filed Nov. 7, 2008, which is incorporated herein by reference in its entirety.

The present application may be related to subject matter disclosed in the following applications, the contents of which are incorporated herein by reference as though set forth in full for all purposes: U.S. patent application Ser. No. 11/073,363, filed on Mar. 4, 2005; U.S. patent application Ser. No. 11/481,433, filed on Jul. 3, 2006; and U.S. patent application Ser. No. 11/804,585, filed on May 17, 2007.

FIELD OF INVENTION

The present invention relates generally to robotically controlled systems, such as robotic or telerobotic surgical systems, and more particularly to mechanical and electrical interface apparatuses that allow transfer or relay of mechanical and electrical input/output from one portion of a robotic system to another portion of the robotic system.

BACKGROUND

In robotically-assisted or telerobotic surgical systems, the surgeon typically operates a master input driver (MID) or master input controller to remotely manipulate, articulate, or control the motion of surgical instruments at the surgical site. The surgeon may be located remotely away from the patient in a different part of the operating room, in a different room, or in a different building. In some applications, the surgeon may be located in a different geographical region away from where the patient is located. The master input driver usually includes one or more manual input devices, such as a mouse, keyboard, trackball, joystick, data gloves, or exoskeletal gloves or the like, which may be coupled to the surgical instruments or tools by way of various linkages, such as wire and/or wireless linkages including connectors, receivers, wires, cables, electrical motors, servo motors, gears, pulleys, etc. for manipulating, articulating, and controlling the surgical instruments or tools. The electrical motors or servo motors are typically part of an electromechanical device, instrument driver, or robotic catheter manipulator (RCM) that supports and controls the surgical instruments and tools for performing various surgical procedures in a patient. In particular, when the robotically-assisted or telerobotic surgical systems are used for minimally invasive surgical procedures, the electromechanical device, instrument driver, or robotic catheter manipulator advances, steers, and/or articulates various surgical instruments, such as steerable catheters, into various body structures and along with various surgical tools, such as ablation catheters, laser catheters, endoscopes, cutters, graspers, lassos, etc. to perform various diagnostic and/or therapeutic treatments on tissue structures inside a patient.

In order to maintain a sterile field or sterile environment for a surgical procedure, a sterile drape is typically used as a barrier between the electromechanical device, instrument driver, or robotic catheter manipulator and the surgical instruments and surgical tools that may be used in the surgical procedures. The sterile drapes used to cover the instrument driver typically include holes or openings through which instruments and tools are coupled to the instrument driver; as such, this type of barrier may not be completely effective in providing a sterile barrier or sterile boundary. Consequently, some portions of the instruments or tools may be exposed to the non-sterile environment, and some portions of the surgical instruments or tools may come in contact with non-sterile components. As a result, at least some portion of the surgical instruments or tools may become contaminated or non-sterile.

Accordingly, improved systems and methods are needed to prevent exposure or contamination of surgical instruments and tools.

SUMMARY

In accordance with one embodiment, a robotic surgical system is configured to perform minimally invasive surgical procedures through remote control by a surgeon. The robotic surgical system includes an instrument driver configured to manipulate an instrument of an instrument assembly in one or more degrees of motion. A drape is disposed between the instrument driver and the instrument assembly; wherein the drape separates a first operational environment from a second operational environment. A drive interface apparatus may be operatively coupled to the instrument driver and the instrument assembly through an opening in the drape. The drive interface apparatus may be disposed on a top surface of the instrument driver and a bottom surface of the instrument assembly. The drive interface apparatus may be configured to transmit torque from the instrument driver to the instrument assembly. The input torque drives at least one pulley in the instrument assembly that operates one or more control wires to manipulate an instrument of the instrument assembly for perform minimally invasive surgical procedures.

According to another embodiment, a robotic surgical system configured to perform minimally invasive surgical procedures through remote control by a surgeon. The robotic surgical system includes an instrument driver configured to steer an elongate instrument of an instrument assembly in one or more degrees of motion. A drape is disposed between the instrument driver and the instrument assembly. A drive interface apparatus is operatively coupled to the drape; wherein the drape and drive interface apparatus form a fluid tight barrier between the instrument driver and the instrument assembly. The drive interface apparatus may be disposed on a top surface of the instrument driver and on a bottom surface of the instrument assembly. The drive interface apparatus is configured to transmit torque from the instrument driver to the instrument assembly. The input torque drives at least one pulley in the instrument assembly that operates one or more control wires to steer the elongate instrument of the instrument assembly for performing minimally invasive surgical procedures.

According to another embodiment, a sterile drive interface apparatus for forming a sterile barrier between a sterile operational environment and a non-sterile operational environment and for transferring motion from an instrument driver to a splayer assembly, e.g., without breaking the sterile barrier, is provided. The sterile drive interface apparatus may include one or more spline shafts. A flange may extend from or be connected to the spline shaft. The flange may have one or more fins positioned on the flange and the fins may be separated by a gap. The sterile drive interface apparatus may further include a drape having a sterile surgical surface with one or more fins positioned thereon. The drape may have a shield positioned on the sterile surgical surface. The one or more fins on the drape may be positioned on the shield, and the fins may be separated by a gap. The shield and/or drape may be configured to receive the spline shaft, where the gaps between shield fins may be configured to receive flange fins and/or the gaps between flange fins may be configured to receive shield fins, such that the flange and/or spline shaft are rotatable relative to the shield and/or drape in a manner of reduced friction. A shield fin and flange fin may form a seal or barrier between the sterile operational environment and the non-sterile operational environment.

Other and further features and advantages of embodiments of the invention will become apparent from the following detailed description, when read in view of the accompanying figures.

BRIEF DESCRIPTION OF THE DRAWINGS

The present invention will be readily understood by the following detailed description, taken in conjunction with accompanying drawings, illustrating by way of examples the principles of the invention. The objects and elements in the drawings are not necessarily drawn to scale, proportion or precise orientation or positional relationship; instead, emphasis is focused on illustrating the principles of the invention. The drawings illustrate the design and utility of various embodiments of the present invention, in which like elements are referred to by like reference symbols or numerals. The drawings, however, depict the embodiments of the invention, and should not be taken as limiting its scope. With this understanding, the embodiments of the invention will be described and explained with specificity and detail through the use of the accompanying drawings in which:

FIG. 2A and FIG. 2B illustrate one embodiment of an instrument driver and instrument assembly.

FIG. 3A and FIG. 3B illustrate one embodiment of an instrument driver.

FIG. 5A and FIG. 5B illustrate one embodiment of splayer and drive interface apparatus.

FIG. 9E and FIG. 9F illustrate one embodiment of a drive pin and drive shaft.

FIG. 11A through FIG. 11H illustrates various embodiments of an interface apparatus or sterile interface apparatus.

FIG. 12A illustrates one embodiment of splayer assembly and sterile drive interface apparatus.

FIG. 12B illustrates an exemplary embodiment of a sterile drive interface apparatus coupled to a splayer assembly and an instrument driver.

FIG. 12C through 12E illustrate top, bottom, and side perspective views of one embodiment of a sterile drive interface apparatus.

FIG. 14A illustrates an exemplary splayer assembly.

FIG. 14B illustrates an exemplary robotic surgical system.

FIG. 14C through 14D illustrate an exemplary spline pulley, with FIG. 14C illustrating an exploded view of the spline pulley.

FIGS. 15A through 15B illustrate an exemplary embodiment of splayer assembly and an exploded view of sterile drive interface apparatus.

DETAILED DESCRIPTION OF ILLUSTRATED EMBODIMENTS

Reference will now be made in detail to the preferred embodiments of the present invention, examples of which are illustrated in the accompanying drawings. While the invention will be described in conjunction with the preferred embodiments, it will be understood that they are not intended to limit the scope of the invention to these embodiments. On the contrary, the invention is intended to cover alternatives, modifications, and equivalents that may be included within the spirit and scope of the invention. Furthermore, in the following detailed description of the present invention, numerous specific details are set forth in to order to provide a thorough understanding of the present invention. However, it will be readily apparent to one of ordinary skilled in the art that the present invention may be practiced without these specific details.

Figure 1:
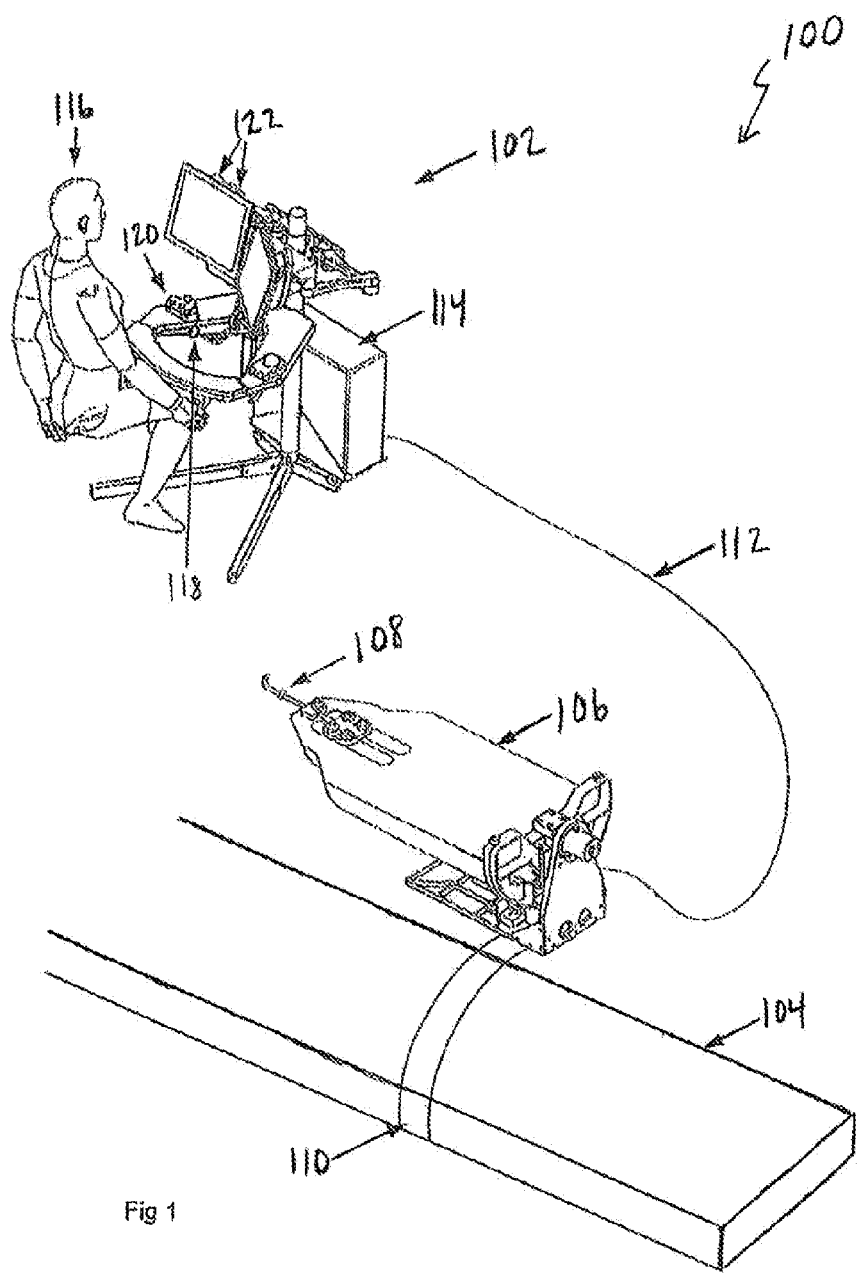
FIG. 1 illustrates one embodiment of a robotic or telerobotic surgical system.

All of the following technologies may be utilized or compatible with manually or robotically steerable instruments, such as those described in the aforementioned U.S. patent application Ser. No. 11/073,363 and U.S. patent application Ser. No. 11/481,433. FIG. 1 illustrates one embodiment of a robotic or telerobotic surgical system (100), e.g., the Sensei™ Robotic Catheter System from Hansen Medical, Inc. in Mountain View, Calif., U.S.A., with an operator control station (102) located remotely from an operating table (104) to which an electromechanical device, instrument driver, or robotic catheter manipulator (RCM) (106) and instrument assembly or steerable catheter assembly (108), e.g., the Artisan™ Control Catheter also from Hansen Medical, Inc. in Mountain View, Calif., U.S.A., may be supported by an instrument driver mounting brace (110) mounted on the operation table (104). A wired connection (112) transfers signals between an electronics rack (114) at the operator control station (102) and the instrument driver (106). The electronics rack (114) includes system hardware and software that operate and perform the many functions of the robotic or telerobotic surgical system (100). The instrument driver mounting brace (110) may be a substantially arcuate-shaped structural member configured to position the instrument driver (106) above a patient (not shown) who is lying on the operating table (104). The wired connection (112) may transmit manipulation, articulation, and control commands from an operator or surgeon (116) who is working at the operator control station (102) and who may be providing the necessary input to the instrument driver (106) by way of one or more input devices, such as an instinctive Motion™ controller (118), joystick, keyboard (120), trackball, data gloves, exoskeletal gloves, or the like, for operating the instrument assembly (108) to perform various operations, such as minimally invasive procedures, on the patient who is lying on the operating table (104). The wired connection (112) may also transmit information (e.g., visual, tactile, force feedback, position, orientation, shape, localization, electrocardiogram, etc.) from the instrument assembly (108), patient, and operation site monitors (not shown in this figure) to the operator control station (102) for providing the necessary information to the operator or surgeon (116) to facilitate monitoring the instruments, patient, and target site for performing various precise manipulation and control of the instrument assembly (108) during the minimally invasive surgical procedure. The wired connection (112) may be a hard wire connection, such as an electrical wire configured to transmit electrical signals (e.g., digital signals, analog signals, etc.), an optical fiber configured to transmit optical signals, a wireless link connection configured to transmit various types of wireless signals (e.g., RF signals, microwave signals, etc.), etc., or any combinations of electrical wire, optical fiber, and/or wireless links. The wire connection (112) allows the surgeon or operator (116) to be remotely located from the patient. The surgeon or operator (116) may be located across the operation room from the patient, in a different room, in a different building, or in a different geographical region away from where the patient is located. Information or feedback transmitted by way of the wire connection (112) may be displayed on one or more monitors (122) at the operator control station (102).

Figure 2A:
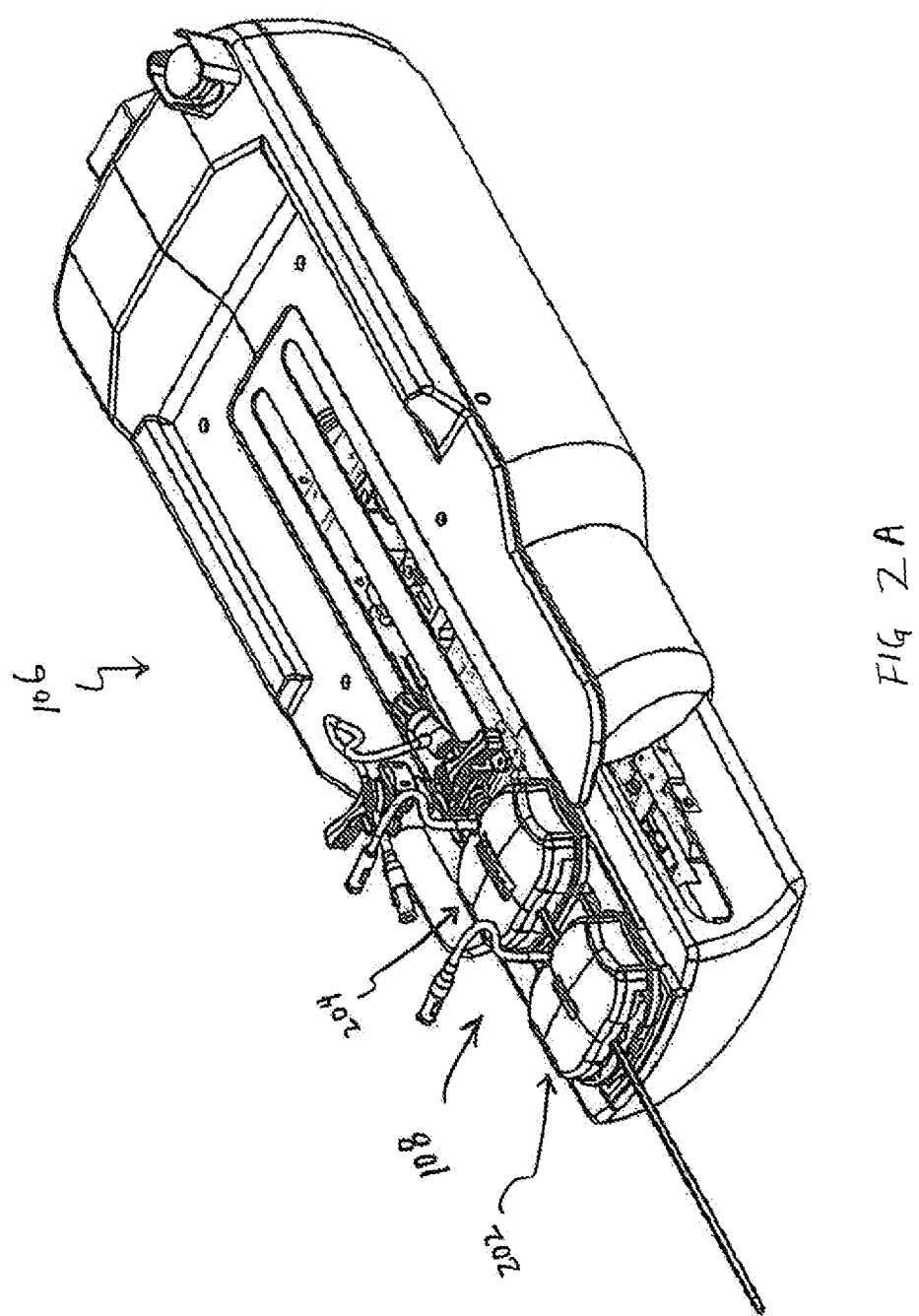

FIG. 2A illustrates one embodiment of an electromechanical device, instrument driver, or robotic catheter manipulator (RCM) (106), which advances, manipulates, articulates, or controls the instrument assembly or steerable catheter assembly (108) based on the command or control input from the surgeon or operator (116) using one more command or control input devices (such as an instinctive motion controller (118) and/or keyboard (120)). When the instrument driver (106) is used to drive the instrument assembly (108), such as advancing and articulating one or more of the steerable catheters of the instrument assembly (108), a sterile drape (not shown) may be placed between the instrument driver (106) and the instrument assembly (108) as a sterile barrier during a surgical procedure. The drape separates a first operational environment from a second operational environment. In other words, the instrument driver (106) may be considered to be a non-sterile component and it may be maintained in a substantially non-sterile environment under the sterile drape, while the instrument assembly (108) and its components may be considered to be sterile components and may be maintained in a substantially sterile environment over the sterile drape. As illustrated in FIG. 2A, the steerable catheter instruments (202 and 204) of the instrument assembly (108) may be positioned in a close together orientation or moved to a far-apart orientation, as illustrated in FIG. 2B, to facilitate removal of either one or both of the steerable catheter instruments (202 and 204) of the instrument assembly (108) from the instrument driver (106). As illustrated in the aforementioned patent applications, the steerable catheter instruments (202 and 204) may be mounted in a co-axial configuration with elongate body of one catheter instrument being threaded through the lumen of another catheter instrument. Accordingly, positioning the catheter instruments in a far-part configuration may facilitate removal of one or both of the catheter instruments from the instrument driver.

FIG. 3A and FIG. 3B illustrate instrument driver (106) with the instrument assembly (108) removed. Referring to FIGS. 2A-2B and FIGS. 3A-3B, the steerable catheter instruments (202 and 204) of the instrument assembly (108) may be respectively mounted and secured onto each of the instrument driver interface plates (302 and 304) of the instrument driver (106). The instrument driver interface plates (302 and 304) may also be referred to as electromechanical device interface plate or robotic catheter manipulator interface plate. The instrument driver interface plates (302 and 304) provide a substantially level surface to which the steerable catheter instruments (202 and 204) of the instrument assembly (108) may be mounted onto the instrument driver (106). Typically, a sterile barrier, such as a sterile drape (402) may be placed between the instrument assembly (108) and the instrument driver (106), as illustrated in FIG. 4.

Figure 4A:
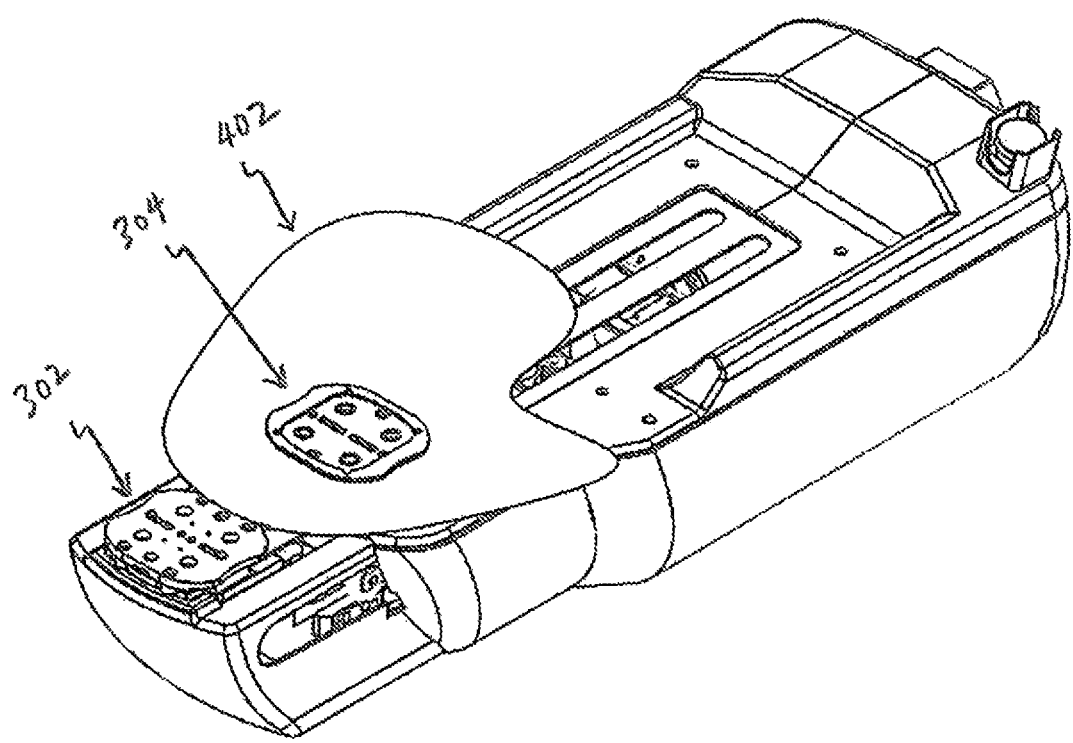
FIG. 4A-4B illustrate one embodiment of an instrument driver and a sterile drape.

In FIG. 4A, a portion of the sterile drape (402) is shown. The sterile drape (402) may be placed over the instrument driver (106) with openings or holes provided on the sterile drape (402) to allow accessibility the instrument driver interface plates (302 and 304), such that the instrument assembly (108) may have contact or may be mounted directly onto the instrument driver (106) through the sterile drape (402).

Figure 4B:
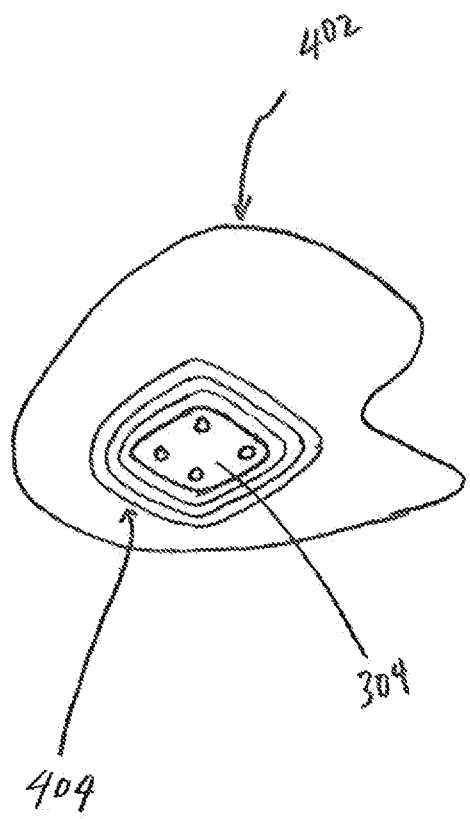

Since the sterile drape (402) has openings or holes, it may not be a complete sterile barrier. To provide more complete barrier, one or more sterile adaptors or drive interface apparatuses (502 and 504) may be added as interfaces between the instrument assembly (108) and the instrument driver (106) to eliminate the need for the sterile components of the instrument assembly (108) to have direct contact with the substantially non-sterile components of the instrument driver (106), as illustrated in FIG. 5A. This way, the components of the instrument assembly (108) may be maintained as sterile components and minimize or eliminate the potential of being contaminated by substantially non-sterile components of the instrument driver (106). In FIG. 5A, the splayer portions (512 and 514) of the steerable catheter instruments (202 and 204) of the instrument assembly (108) are shown. The splayer portions (512 and 514) of the steerable catheter instruments (202 and 204) contain the drive mechanisms that allow steering or articulation of the steerable catheters. FIG. 5B illustrates one of the drive interface apparatus (504) without the splayer assembly (514) attached. The drive interface apparatuses (502 and 504) are mounted directly onto the respective instrument driver interface plates (302 and 304). In this embodiment, only the drive interface apparatuses (502 and 504) are in direct contact with instrument driver interface plates (302 and 304) and the drive mechanisms in the instrument driver (106) through which the drive mechanisms in the splayer assemblies (512 and 514) are driven. The components of the drive interface apparatuses (502 and 504) operate the components of the splayers ((512 and 514) which steer and articulate the steerable catheters of the instrument assembly (108). In some embodiments, the drape (402) may be placed, disposed, or tucked under the drive interface apparatuses (502 and 504); such that the combination of the drape (402) and drive interface apparatuses (502 and 504) form a substantially fluid tight or fluid resistant barrier. In further embodiments, the portions of the drape where contact is made with the drive interface apparatuses (502 and 504) may include sealant material to provide or enhance the substantially fluid tight or fluid resistant property of the combination. In other embodiments, the drive interface apparatuses (502 and 604) may also include sealant material to provide or enhance the substantially fluid tight or fluid resistant property of the combination. In further embodiments, the drape (402) may include grooves or channels (404) to provide or enhance the substantially fluid tight or fluid resistant property of the combination, as illustrated in FIG. 4B.

In some embodiments, the splayer assemblies (512 and 514) may be substantially similar or identical. That is the splayer assemblies (512 and 514) may contain similar components and may be configured in a similar manner. For example, the splayer assemblies (512 and 514) may contain similar drive components to operate the same number of control wires (e.g., 1, 2, 3, 4, etc.) to steer or articulate (e.g., up, down, pitch, yaw, etc.) the steerable catheters of the instrument assembly (108) with similar or same degrees of control for steering or articulating the steerable catheters of the instrument assembly. In other embodiments, the splayer assemblies (512 and 514) may not be substantially similar or identical. That is, one splayer assembly (e.g., 512) may contain fewer components than the other splayer assembly (e.g., 514); such that one splayer assembly (e.g., 512) may contain components that operate fewer control wires than the other splayer assembly (e.g., 514). Consequently, one splayer assembly (e.g., 512) may be able to steer or articulate a steerable catheter in limited or fewer directions than the other splayer assembly (e.g., 514).

Figure 6A:
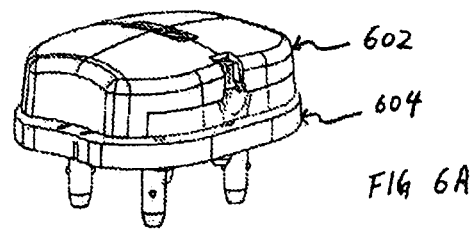
FIG. 6A through FIG. 6D illustrate the components of an exemplary splayer assembly and drive interface apparatus.
Figures 6B, 6C:
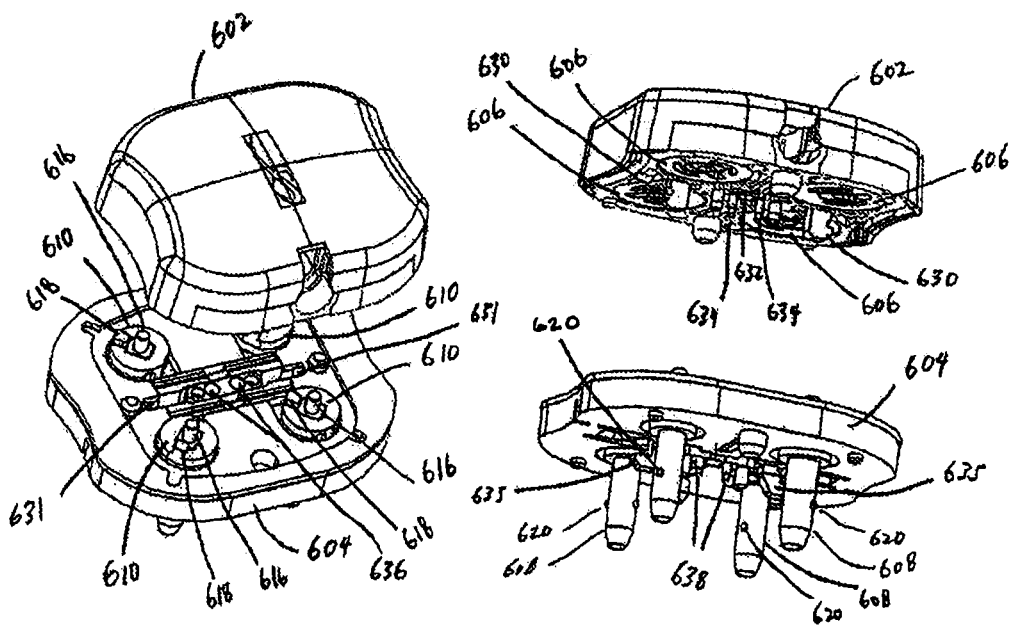
Figure 6D:
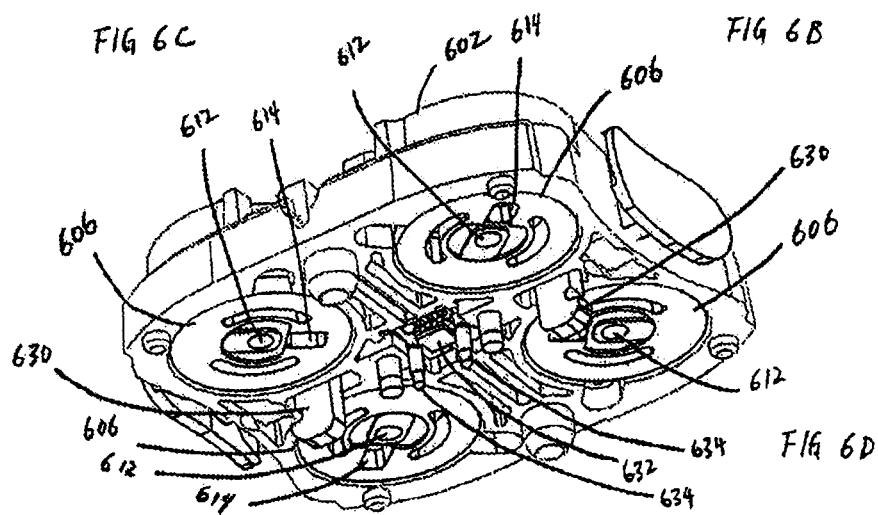

FIG. 6A through FIG. 6D illustrate one embodiment of a splayer assembly (602) and one embodiment of a drive interface apparatus (604). As illustrated in FIG. 6B and FIG. 6D, the splayer assembly (602) comprises of four drive mechanisms or drive pulleys (606) to operate control wires (not shown) to steer or articulate a steerable catheter in various directions (e.g., up, down, pitch, yaw, etc.). In addition, the splayer assembly may include an identification chip or circuitry (632) which may contain product information (e.g., serial number, date of manufacture, code key, etc.) of the instrument assembly (108), and an identification pin connectors (634) may be plugged into pin receivers (636) in the drive interface apparatus (604) for wired connection or interface. In other embodiments, the chip or circuitry (632) may not require wire connections; instead, it may communicate with other chips or circuitry in a wireless manner. For example, the chip (632) may be a solid-state RF integrated circuit (IC) that is configured to communicate with other circuits by RF transmission signals. The chip or circuitry (634) may be configured to transmit and receive signals in the range of about 5 MHz to about 20 MHz. The signals may be in the range of about 5 mWatts to about 15 mWatts. In a preferred embodiment, the circuitry (634) may be configured to transmit and receive signals at about 13 MHz. The signals may be in the range of about 10 mWatts.

Continuing with the current example, the splayer assembly may also includes latch hooks (630) for engaging or mounting the splayer assembly to the drive interface apparatus (604) by way of the latch receivers (631). Additionally, FIG. 6B illustrates the bottom portion of the drive interface apparatus (604) in which four drive pins (608) are used to engage drive mechanisms in the instrument driver (106) as drive input for operating the drive pulleys (606) in the splayer assembly (602) that translate operation of the drive pulleys (606) to steering or articulating the steerable catheter. The drive interface apparatus (604) may also include lead pins (638) for relaying the electrical signals or data transmitted from the identification chip or circuitry (632) to the instrument driver (106), which may be relayed to the electronics rack (114) and displayed to the operator or surgeon (116) on the monitors (122). The instrument driver (106) may also include circuitry configured to transmit and receive signals in the range of about 5 MHz to about 20 MHz. The signals may be in the range of about 5 mWatts to about 15 mWatts. In a preferred embodiment, the circuitry of the instrument driver may be configured to transmit and receive signals at about 13 MHz. The signals may be in the range of about 10 mWatts.

In one variation, the splayer assembly includes an RFID chip that carries product information (e.g., model number, production serial number, etc.) and/or product specification (e.g., sizing information of the robotic catheter coupled to the slayer, calibration data, etc.). The instrument driver includes an RFID chip reader capable of providing excitation energy to the RFID chip, and detecting signal from the RFID chip to read the data contained on the RFID chip. In another variation, a RF integrated circuit is positioned on the splayer and a corresponding reader circuit is positioned on the instrument driver, such that when the user engage the splayer onto the instrument driver, the instrument driver can verify that the splayer has fully aligned and docked onto the instrument driver through signal received from the RF integrated circuit.

In another variation, the splayer includes one or more magnets, and the instrument driver includes one or more detectors to detect the position of the magnets, such that the instrument driver is able to verify that the splayer is properly aligned and/or docked onto the instrument driver.

In yet another variation, a portion of the drape positioned between the splayer and the instrument driver includes one or more areas having materials that are optically transparent or semi-transparent (i.e., transparent window). The instrument driver includes an optical reader (e.g., digital camera/detector, bar code reader, etc.) capable of reading information provided on the bottom surface of the splayer through the transparent window-on the drape when the splayer is fully docked onto the instrument driver. Indicia may also be provided on the underside of the splayer such that the optical reader can verify alignment and/or docking of the splayer. Alternatively, the instrument driver includes an optical excitation source (e.g., laser) positioned to transmit photons through the transparent window on the drape and onto a reflective medium on the splayer. Through an optical receiver located on the instrument driver, the instrument driver can then verify that the splayer is aligned and/or fully docketed on the instrument driver. The reflective medium may also carry product information and product specification, such that the reflected energy captured by the optical receiver can decode the information carried by the reflect energy to identify the splayer being mounted on to the instrument driver by the user.

As may be appreciated by one of ordinary skill in the art, the circuit (632) may communicate with other circuits by optical signals instead of electrical signals or the circuit (632) may communicate with other circuits by a combination of electrical and optical signals; by wire, wireless, or combination of wire and wireless links. In addition, the drive interface apparatus (604) also includes latch hooks (635) for latching the drive interface apparatus (604) to the instrument driver interface plate (i.e., 302 and 304). FIG. 6C illustrates the top portion of the drive interface apparatus (604) in which flexture engagement features (610) are shown. The flexture engagement feature (610) is the engagement portion of the drive pin (608) that engages with the drive pulley (606) of the splayer assembly (602). In this figure, the latch receivers (631) and pin receivers (636) are also visible. FIG. 6D illustrates the bottom portion of the splayer assembly (602) in which the features of the drive pulleys (606) are more clearly illustrated. For example, the female mating features of the female axial cavity (612) and the female mating torque cavity (614) are more clearly illustrated in FIG. 6D; whereas the male mating features of the male axial knob (616) and the male torque knob (618) are more clearly illustrated in FIG. 6C. Furthermore, the drive pins (608) of the drive interface apparatus (604) include male torque knobs (620) that engage with the drive mechanisms in the instrument driver (106). Essentially, through these mating features of the mating components, rotation or torque input from the instrument driver (106) may be transmitted through the drive interface apparatus (604) to the splayer assembly (602). The transmitted torque drives one or more drive pulleys (606) of the splayer assembly (602), which operate one or more control wires (not shown) that steer or articulate the steerable catheter of the instrument assembly (108). In addition, information from the identification chip from the splayers of the instrument assembly (108) may be downloaded from the splayers through the instrument driver (106) to the operator control station (102).

A passcode from the operator or surgeon may be required to operate the splayer assembly. The drive interface apparatus (604) may be operated as a sterile interface between the instrument driver (106) and the instrument assembly (108). Since the sterile components of the instrument assembly (108) do not contact with the substantially non-sterile components of the instrument driver (106), the potential for contaminating the sterile components of the instrument assembly (108) may be minimized or eliminated. The splayer assembly (602) and the drive interface apparatus (604) may be made from any bio-compatible material and/or sterilizable material, e.g., stainless steel, Nitinol, polycarbonate compounds, etc.

Figure 7A:
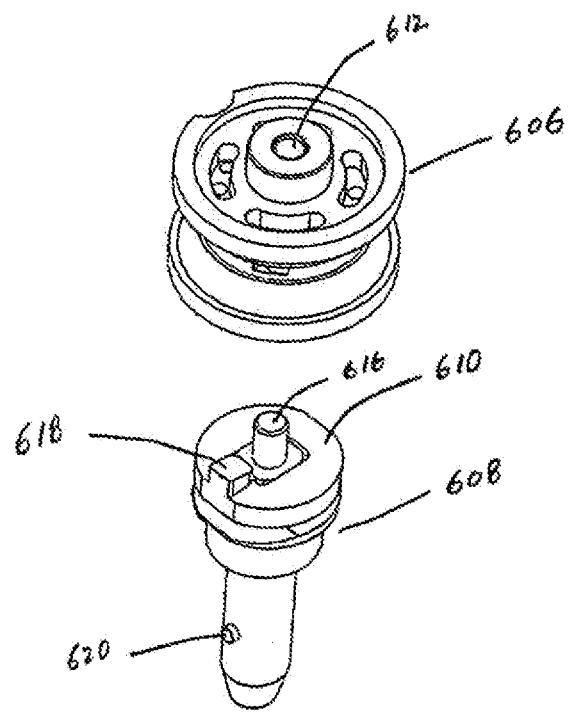
FIG. 7A and FIG. 7B illustrate the exemplary drive components of a splayer assembly and drive interface apparatus.
Figure 7B:
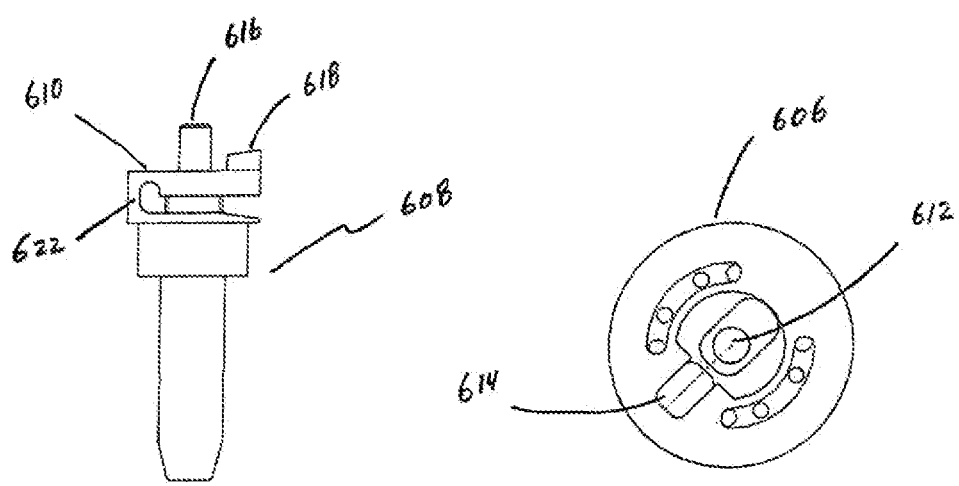

FIG. 7A and FIG. 7B illustrate close-up views of the drive pulley (606) of the splayer assembly (602) and the drive pin (608) of the drive interface apparatus (604). Referring to the flexture engagement feature (610) in FIG. 7B, this flexture feature may be fabricated with a cantilever type construction or configuration, such that it may be flexed, bent, pivoted, or floated relatively freely about a flexture region (622). In particular, the flexture feature (e.g., the ability to flex, bent, pivot, float, etc.) may allow greater flexibility or tolerance when mating the drive pin (608) to the drive pulley (606). That is, when the splayer assembly (602) is pressed onto the drive pin (608) or the drive interface apparatus (604), the flexture feature allows the drive pin head to flex, bend, pivot, or float relatively freely such that sufficient tolerance may be available to allowed for the splayer assembly (602) to be fitted onto the drive interface apparatus (604) even though the male and female mating features may not be substantially aligned. The male and female mating features may become aligned once the drive pin (608) is rotated by the instrument driver (106), if they were not initially aligned. The flexture feature will snap or engage the male mating feature into the female mating feature as the mating features become aligned, e.g., as the drive pin is rotated.

Figure 8A:
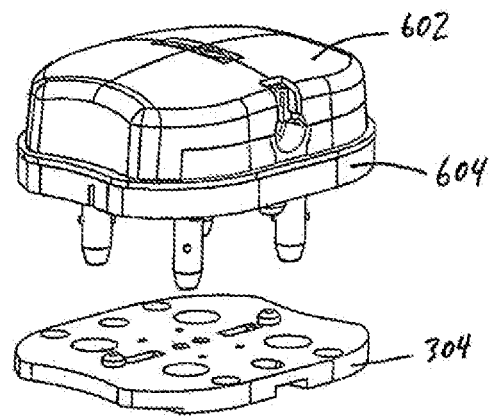
FIG. 8A through FIG. 8C illustrate an exemplary combination of splayer assembly, drive apparatus, and instrument driver interface plate.
Figure 8B:
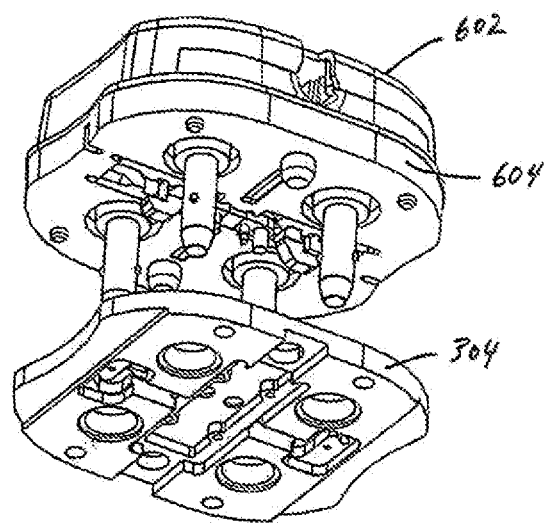
Figure 8C:
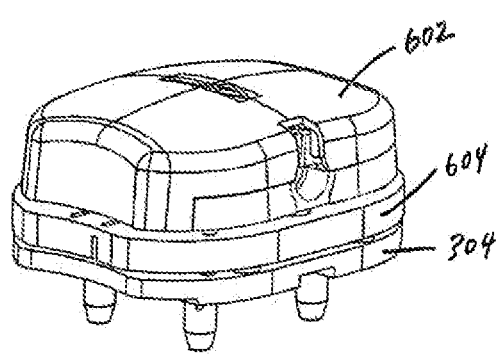

FIG. 8A through FIG. 8C illustrate the assembly of a splayer (602), a drive interface apparatus (604), and an instrument driver interface plate (304). As can be seen from the figures, these components or assemblies are designed to fit and mate together in a substantially seamless or fitted manner. In one embodiment, the drive interface apparatus (604) may be mounted onto the instrument driver interface plate (304). For example, the bottom surface of the drive interface apparatus (604) would contact the top surface of the instrument driver interface plate (304). The splayer (602) may be mounted onto the drive interface apparatus (604), such that the bottom surface of the splayer (602) would contact the top surface of the drive interface apparatus (604). The splayer (602), drive interface apparatus (604), and instrument driver interface plate (304) are intended to be assemble together and operated substantially as a unit.

Figure 9A:
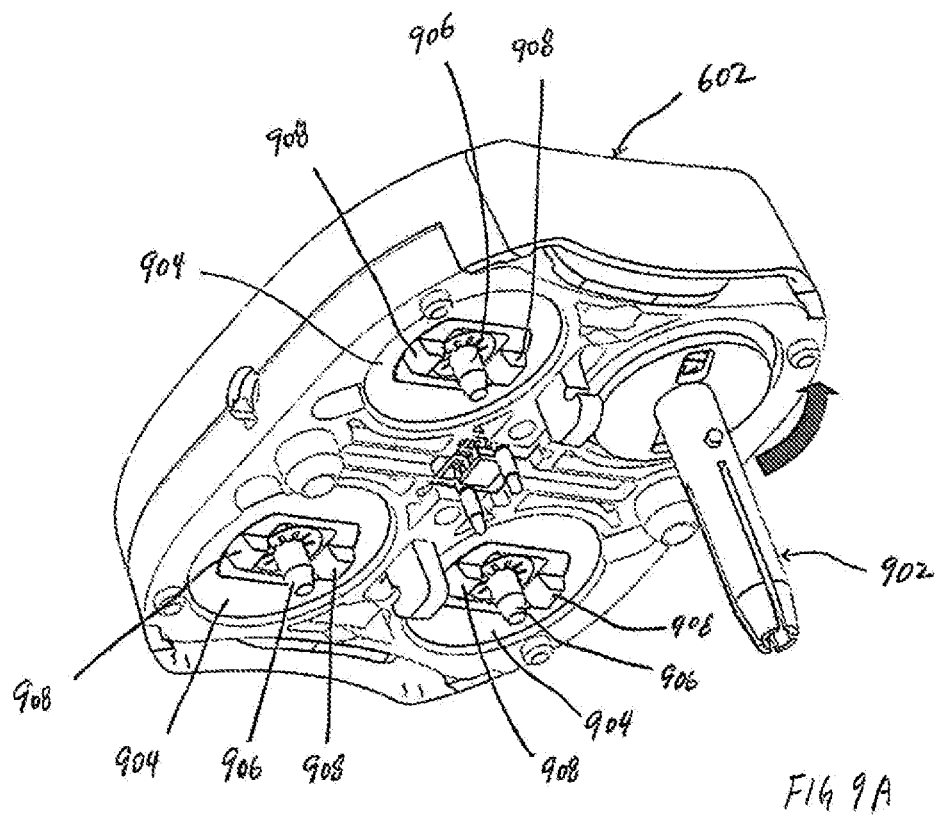
FIGS. 9A and 9B illustrate an embodiment of a splayer assembly and drive interface apparatus.
Figure 9B:
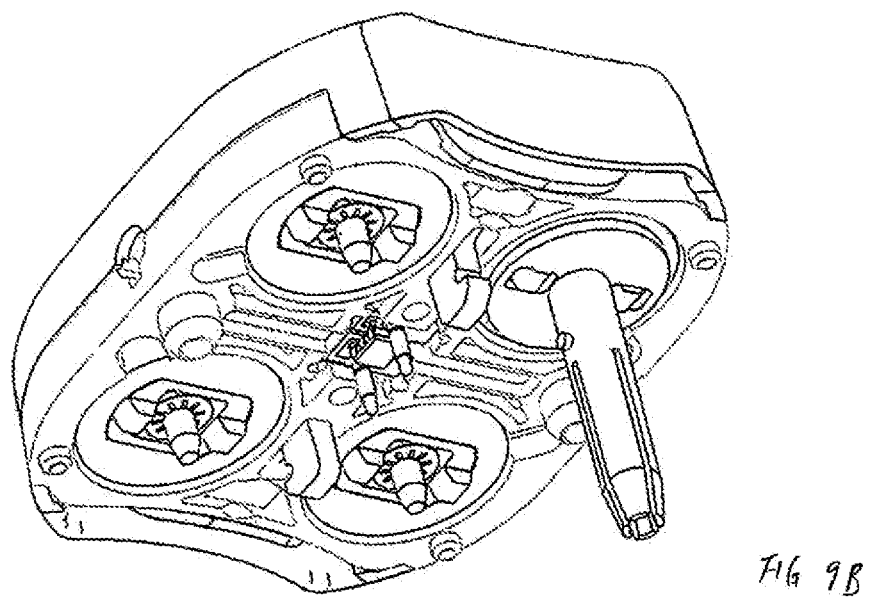
Figure 9C:
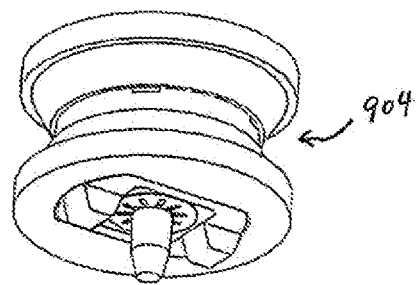
FIG. 9C and FIG. 9D illustrate one embodiment of a drive pulley.
Figure 9D:
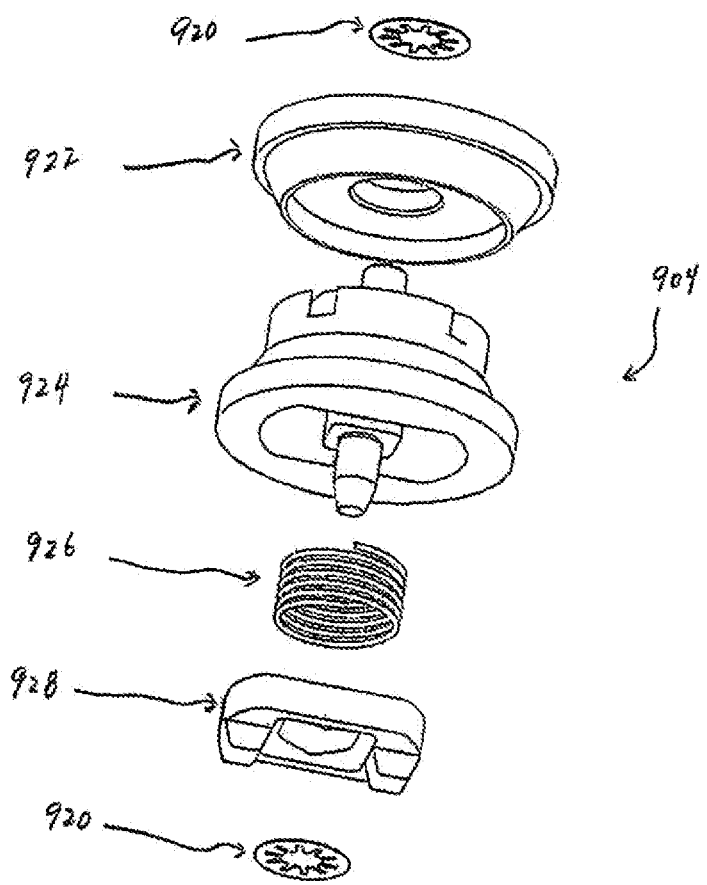

FIG. 9A through FIG. 9F illustrate another embodiment of a drive interface apparatus and the corresponding mating elements of the splayer assembly and instrument driver. FIG. 9A illustrates one embodiment of a drive pin (902) which transmits torque from the instrument driver (106) to the splayer assembly (602). FIG. 9A also illustrates one embodiment of a drive pulley (904) which is designed or configured to mate with the drive pin (902) and operate one or more control wires to steer or articulate a steerable catheter. In this embodiment, the drive pulley (904) includes male mating features, such as male axial knob (906) and male torque knobs (908), that mate with female mating features, such as female axial cavity (910) and female torque cavities (912), of the drive pin (902). In this embodiment, the drive pulley (904) may be designed or configured to be spring loaded, as illustrated in FIG. 9D, such that portion of the drive pulley (904), e.g., gimble (928), may be allowed to float, pivot, depress, or give. As such, drive pulley (904) may have a pressed or spring loaded contact with the drive pin (902) even when the mating features of the drive pulley (904) may not be substantially or completely aligned with the mating features of the drive pin (902). As the drive pin (902) is rotated, the mating features may become aligned. FIG. 9C illustrates one example of a drive pulley (904). FIG. 9D illustrate the details of one embodiment of a drive pulley (904). As illustrated, drive pulley (904) includes retainers (920), capstan cap (922), capstan (924), spring (926), and gimble latch (928). In combination with the spring (926), the gimble latch is a substantially free floating mechanism that is allowed to float, pivot, etc. within the capstan (924).

Referring back to FIG. 9A and FIG. 9B, the respective male and female mating features of the drive pulleys (904) and the drive pins (902) may become aligned once the drive pins (902) are rotated by the instrument driver (106). The spring feature of the gimble latch (928) of drive pulley (904) will snap or engage the male mating features into the female mating features as the mating features become aligned, e.g., when the drive pins are rotated. FIG. 9A illustrates that as the drive pulley (904) comes into contact with the drive pin (902), the mating features may not be initially aligned when they are mounted together. The drive pin (902) may be rotated, as indicated by the arrow. The female mating features of the drive pin (902) may become aligned with the male mating features of the drive pulley (904) after the drive pin (902) is rotated, as illustrated in FIG. 9B. The male mating features of the drive pulley (904) may snap into or fit into the female mating features of the drive pin (902) as the features become aligned.

FIG. 9E and FIG. 9F illustrate how the drive pin (902) may be mated with drive component of the instrument driver (106). The instrument driver (106) may include a drive or torque output shaft (914) in which the drive pin (902) may engage by way of the shaft receptor (916). The shaft receptor may include a slot or groove (918) to engage a torque knob (920) of the drive pin (902) to facilitate transmission of torque output from the torque shaft (914) to the drive pin (902). Through these mating features of the mating components, rotation or torque input from the instrument driver (106) is transmitted through the drive interface apparatus (902) to the splayer assembly (602). The transmitted torque drives the drive pulleys (904) of the splayer assembly (602), which operate control wires (not shown) that steer or articulate the steerable catheter of the instrument assembly (108). As such, the drive interface apparatus (902) may be operated as a sterile interface between the instrument driver (106) and the instrument assembly (108). Since the sterile components of the instrument assembly (108) do not contact with the substantially non-sterile components of the instrument driver (106), the potential for contaminating the sterile components of the instrument assembly (108) is therefore substantially minimized or eliminated. The splayer assembly (602) and the drive interface apparatus (902) may be made from any bio-compatible material and/or sterilizable material, e.g., stainless steel, Nitinol, polycarbonate compounds, etc. FIG. 9F illustrates how a drive pin (902) may engage the instrument driver (106) in accordance with this embodiment. As shown, the tip portion of the drive pin (902) is fitted into the shaft receptor cavity (916) of the torque shaft (914). The torque knob (920) of the drive pin (902) engages or is fitted into the slot or groove (918) of the torque shaft (914), such that the output torque from the torque shaft (914) may be transmitted to the drive pin (902). Subsequently, the drive pin (902)

rotates or transmits torque to the drive pulley (904) which operates at least one pull wire that steers or articulates a steerable catheter of the instrument assembly (108).

Figure 10A:
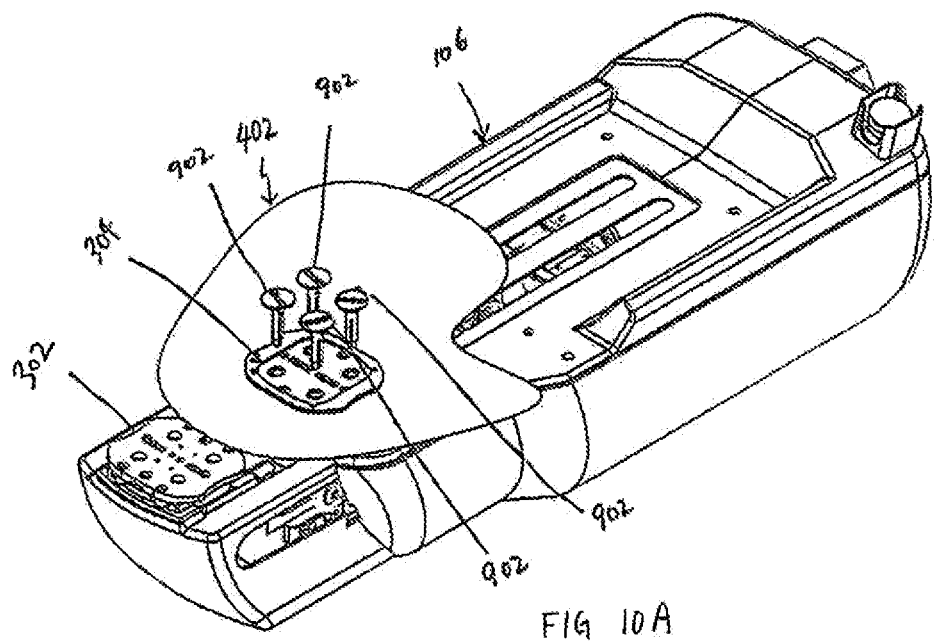
FIG. 10A and FIG. 10B illustrate an exemplary combination of a sterile drape and drive pin installed onto an instrument driver.
Figure 10B:
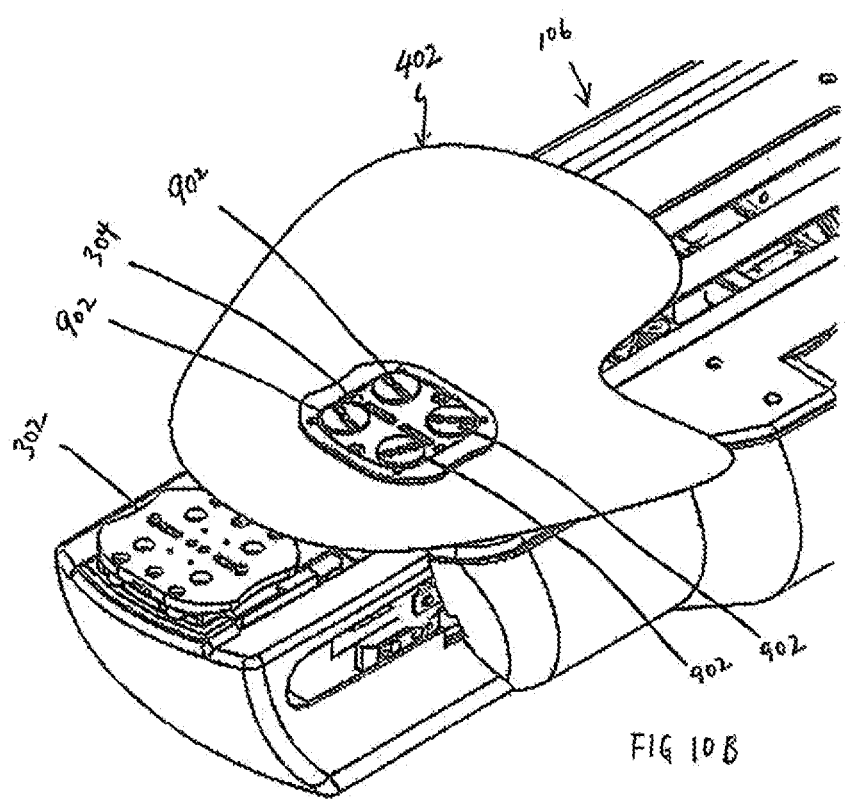

FIG. 10A and FIG. 10B illustrates how the drive pins (902) may be placed into the instrument driver (106). As illustrated in FIG. 10A and FIG. 10B, a portion of a sterile drape (402) is shown covering the instrument driver (106) to provide a sterile barrier. The drive pins (902) may be inserted through the driver interface plates (302 and 304). For convenience and clarity, FIG. 10A and FIG. 10B only illustrate the drive pins (902) being inserted through one of the driver interface plates (e.g., 304) to engage with the drive shaft receptor cavity (916) of the output torque shaft (914) in the instrument driver (106).

Figure 11B:
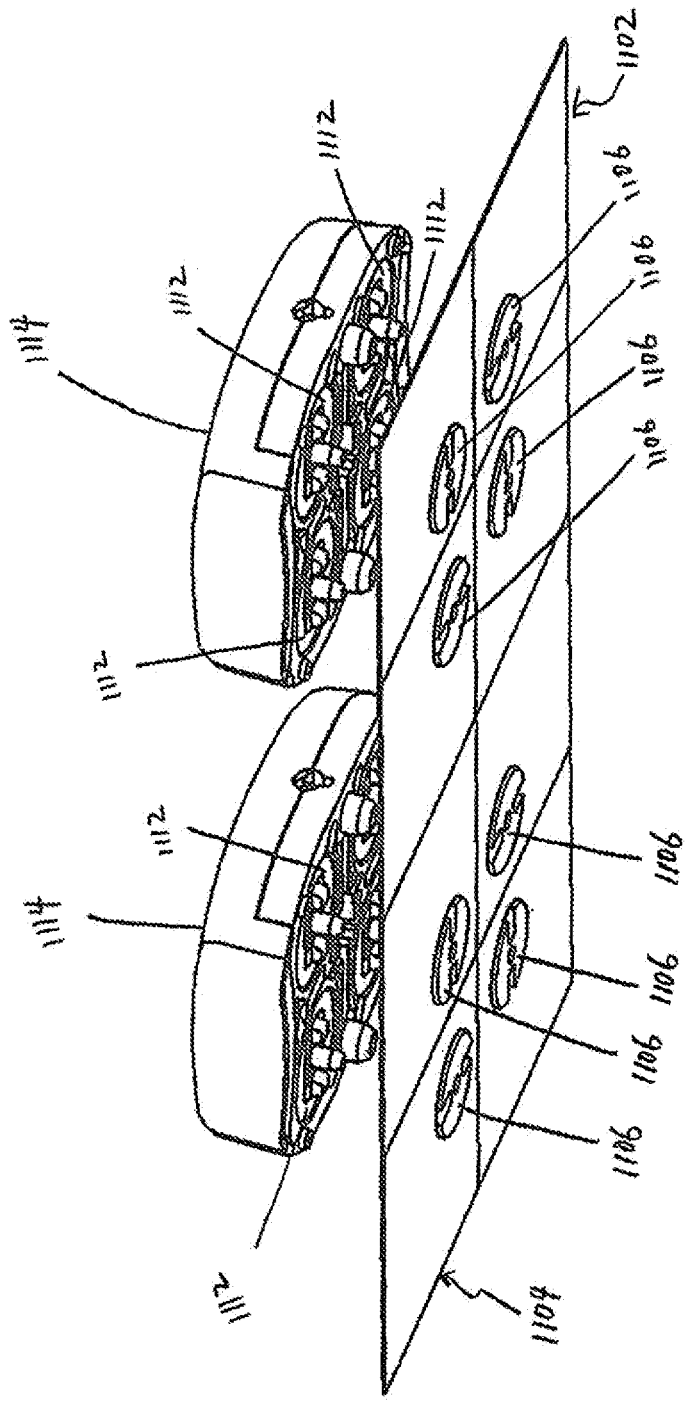
Figure 11C:
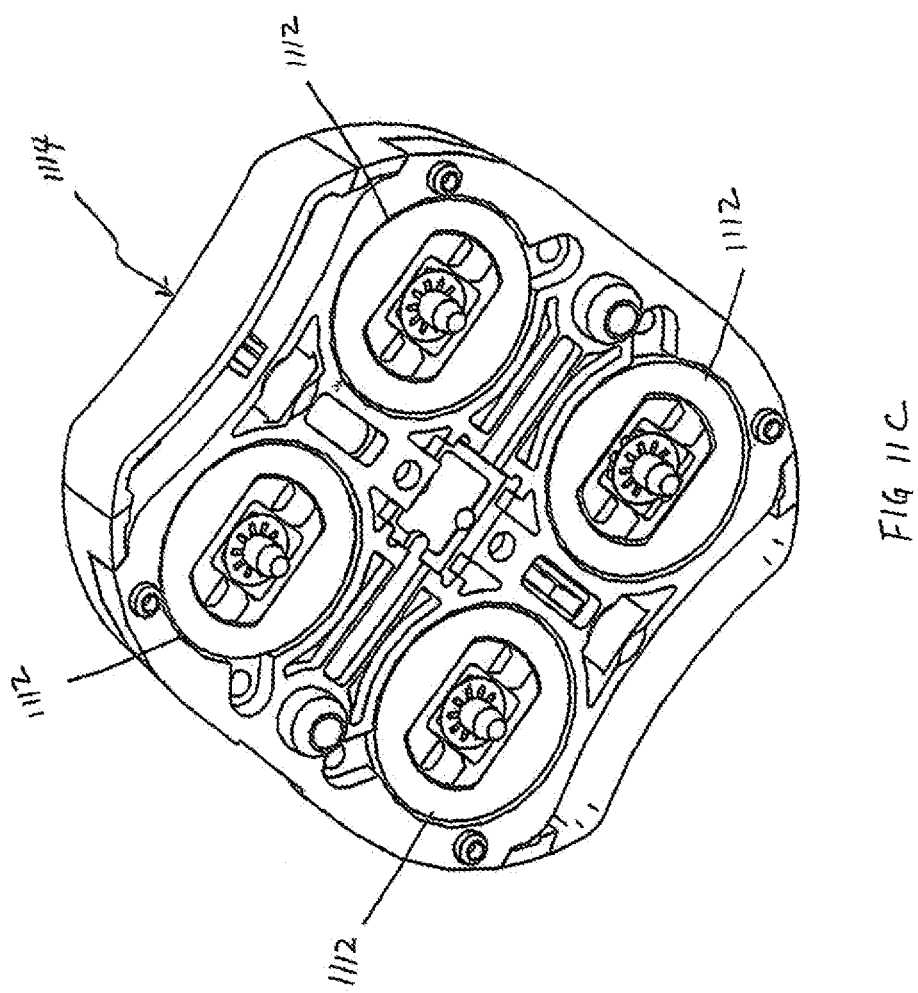

FIG. 11A through FIG. 11C illustrate another embodiment of a drive interface apparatus or sterile interface apparatus (1102). For this embodiment, the sterile interface apparatus (1102) includes a drape (1104) and one or more drive transmission apparatuses (1106). In this example, the sterile interface (1102) includes four drive transmission apparatuses (1106). The drive transmission apparatuses (1106) are configured to interface with the drive gears (1108) of the instrument driver interface plate (1110) and the driver pulleys (1112) of the splayer assembly (1114). The drive transmission apparatuses (1106), drive gears (1108) of the instrument driver interface plate (1110) and drive pulleys (1112) of the splayer (1114) have mating features or complementary mating features that mate or fit together, such that torque output from the instrument driver (106) may be transmitted by the drive gears (1108) of the instrument driver interface plate (1110) through the drive transmission apparatuses (1106) of the sterile interface apparatus (1102) to the drive pulleys (1112) of the splayer (1114) to operate one or more control wires for steering or articulating a steerable catheter. For example, the mating features on the top surfaces of the drive transmission apparatuses (1106) and the drive gears (1108) can be seen in FIG. 11A, and the mating features on the bottom surfaces of the drive pulleys (1112) and drive transmission apparatuses (1106) can be seen in FIG. 11B. Through the drive transmission apparatuses (1106), the drive pulleys (1112) may be operated by the torque input from the drive gears (1108) of the instrument driver (106) without any of the parts or components of the splayer or instrument assembly or catheter instrument assembly having direct contact with any of the parts or components of the instrument driver. As such, the sterile condition of the catheter instrument assembly may not be affected by the non-sterile condition of the instrument driver.

Figure 11D:
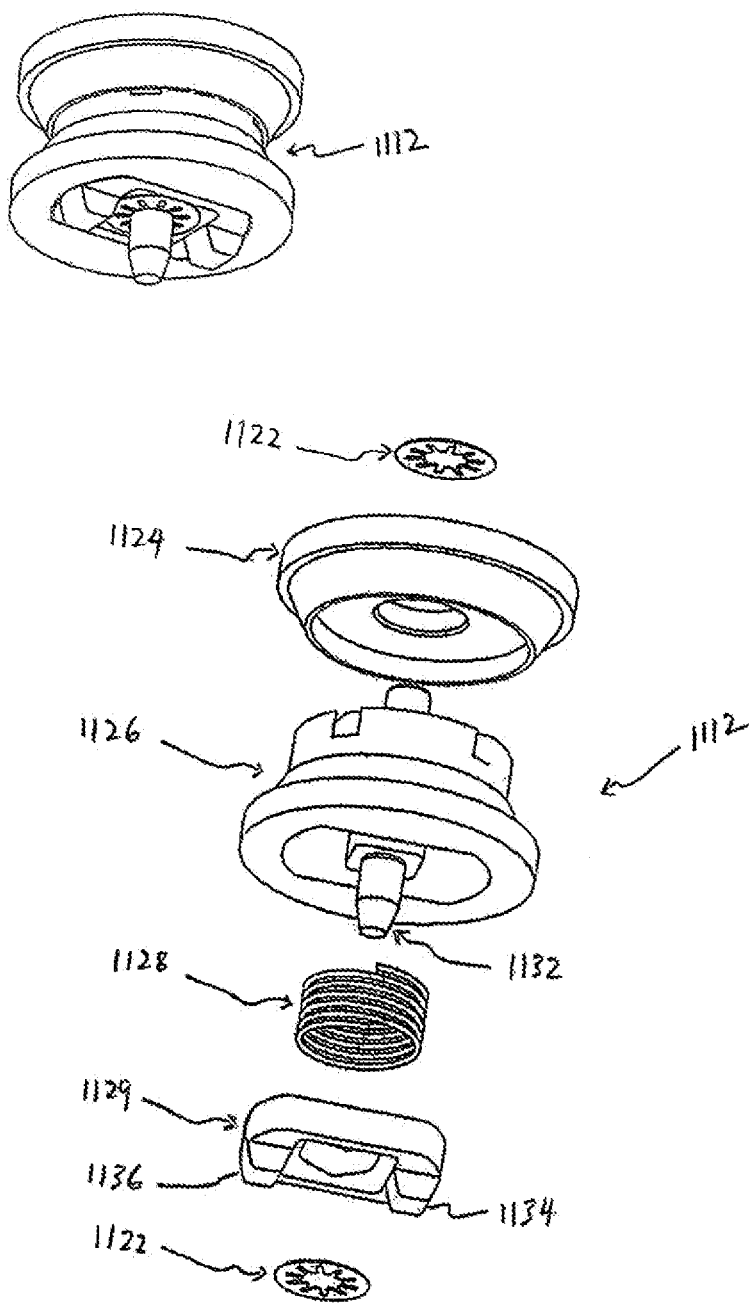
Figure 11E:
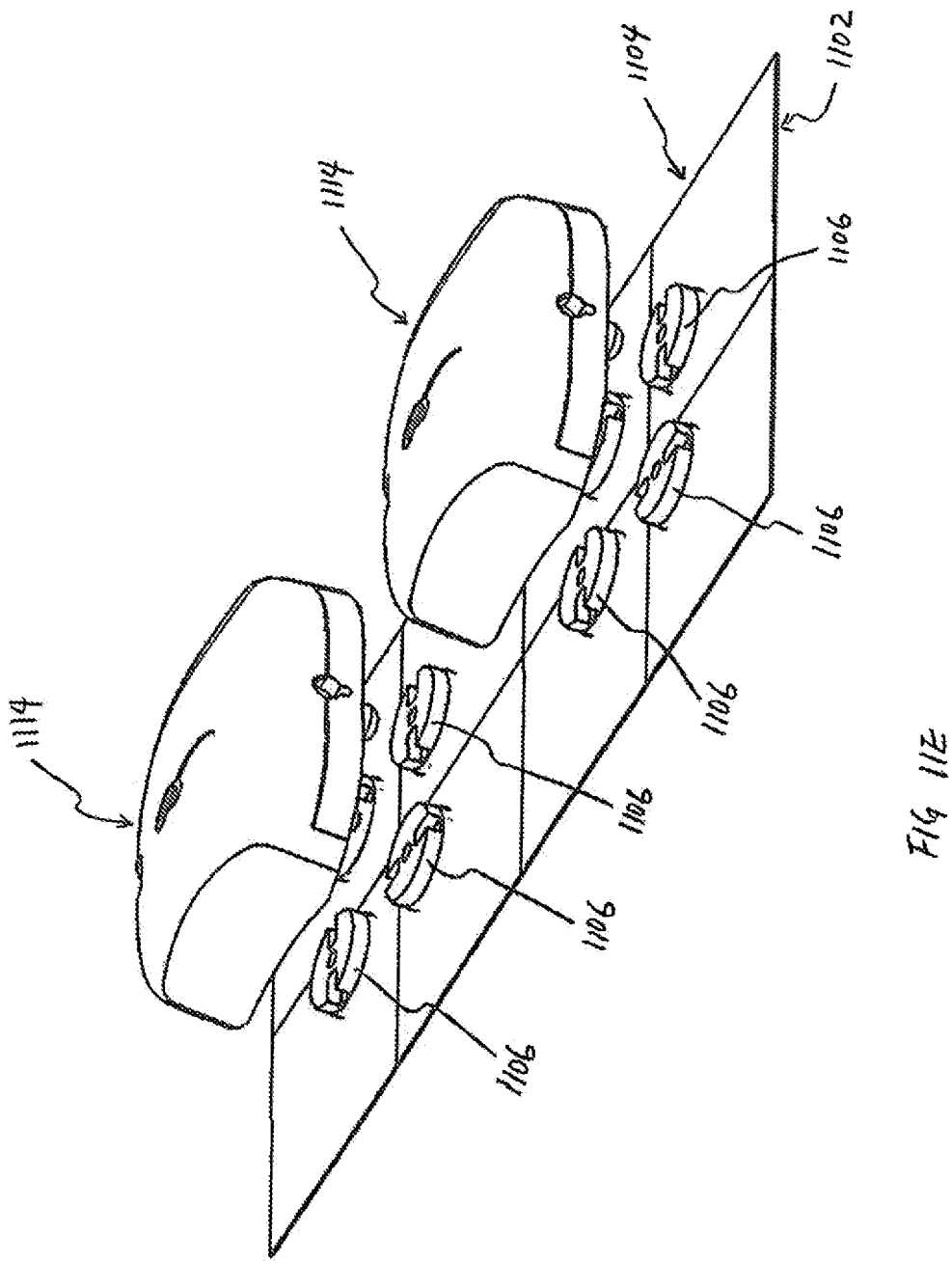

FIG. 11C illustrates a close-up view of the splayer assembly (1114). The splayer assembly (1114) may include a one or more drive pulleys (1112). For example, the splayer assembly (1114) may include four drive pulleys (1112). In one embodiment, a drive pulley (1112) may include retainers (1122), capstan cap (1124), capstan (1126), spring (1128), and gimble latch (1129), as illustrated in FIG. 11D. The combination of the capstan (1126), spring (1128), and gimble latch (1129) allows the mating features of the drive pulley (1112) to float or pivot to facilitate mating or fitting with the mating features of the drive transmission apparatus (1106). If the mating features of the drive pulley (1112) and the drive transmission apparatus (1106) are not initially aligned when placed together, the floating or pivoting features of the drive pulley (1112) may still allow the drive pulley (1112) to mate with drive transmission apparatus (1106). In addition, as the transmission apparatus (1106) is rotated, the mating features may become aligned and would mate or fit together. The drive pulley (1112) may include mating features such as an axial pin (1132), first torque knob (1134) and second torque knob (1136). In some embodiments, the first torque (1134) may be configured substantially similar to the second torque knob (1136). In some other embodiments, the first torque knob (1134) may be substantially dissimilar to the second torque knob (1136). For example, the first torque knob (1134) may be longer than the second torque knob (1136). In addition, the first torque knob (1134) may have a substantially round or elliptical profile, while the second torque knob (1136) may have a substantially rectangular profile. The mating features of the drive pulleys (1112) mate with or fit into the mating features of the drive transmission apparatuses (1106). Similarly, mating features on the drive gears (1108) mate with or fit into the mating features of the drive transmission apparatuses (1106). FIG. 11D illustrates another view of the splayer assembly (1114) and the sterile interface apparatus (1102) in which the mating features of the drive transmission apparatuses (1106) are shown more clearly, in accordance with one embodiment.

Although not illustrated, the splayer assembly (1114) may include wireless circuitry to communicate with circuitry in the instrument driver (106). The wireless circuitry may contain various data related to the splayer assembly (1114). In addition, it may include security features that only allow a user or surgeon with the correct security code or passcode to operate the splayer assembly (1114) and associated instruments. The circuitry of the splayer assembly (1114) and the instrument driver (106) may be solid-state RF circuitry or optical circuitry.

Referring again to FIG. 11A and FIG. 11B, the sterile drape (1104) may be incorporated with the drive transmission apparatuses (1106) to form a substantially fluid tight or fluid resistant barrier. The drape (1104) may be made from any suitable material, such as fluid resistant or fluid proof material or fabric (e.g., plastic, Gore-tex®, etc.). The drape (1104) may be substantially pliable, flexible, stiff, or rigid. In some embodiments, certain portion of the drape (1104) may be substantially pliable or flexible, while another portion of the drape (1104) may be substantially stiff or rigid. The drape (1104) may be constructed from a single layer or sheet of material or fabric. The drape (1104) may also be constructed from multi-layers or multi-sheets of material or fabric. The components on one side of the sterile interface (1102) may be substantially isolated from components on the other side of the sterile interface (1102). For example, the components (e.g., the instrument assembly including the splayer assemblies and catheters) on top surface of the sterile interface (1102) may remain sterile in one operational environment without being affected by the components (e.g., the instrument driver) below the bottom surface of the sterile interface (1102) in another operational environment, which may be non-sterile. In addition, because the sterile interface (1102) may be a substantially fluid tight or fluid resistant barrier, there may not be any exchange or fluid or particles between the environment on one side of the sterile barrier and the environment on other side of the sterile barrier. For example, a sterile environment on the top side of the sterile interface (1102) will remain substantially sterile without being affected or contaminated by the environment on the bottom side of the sterile interface, even if the environment on the bottom side of the sterile interface (1102) is non-sterile.

Figure 11F:
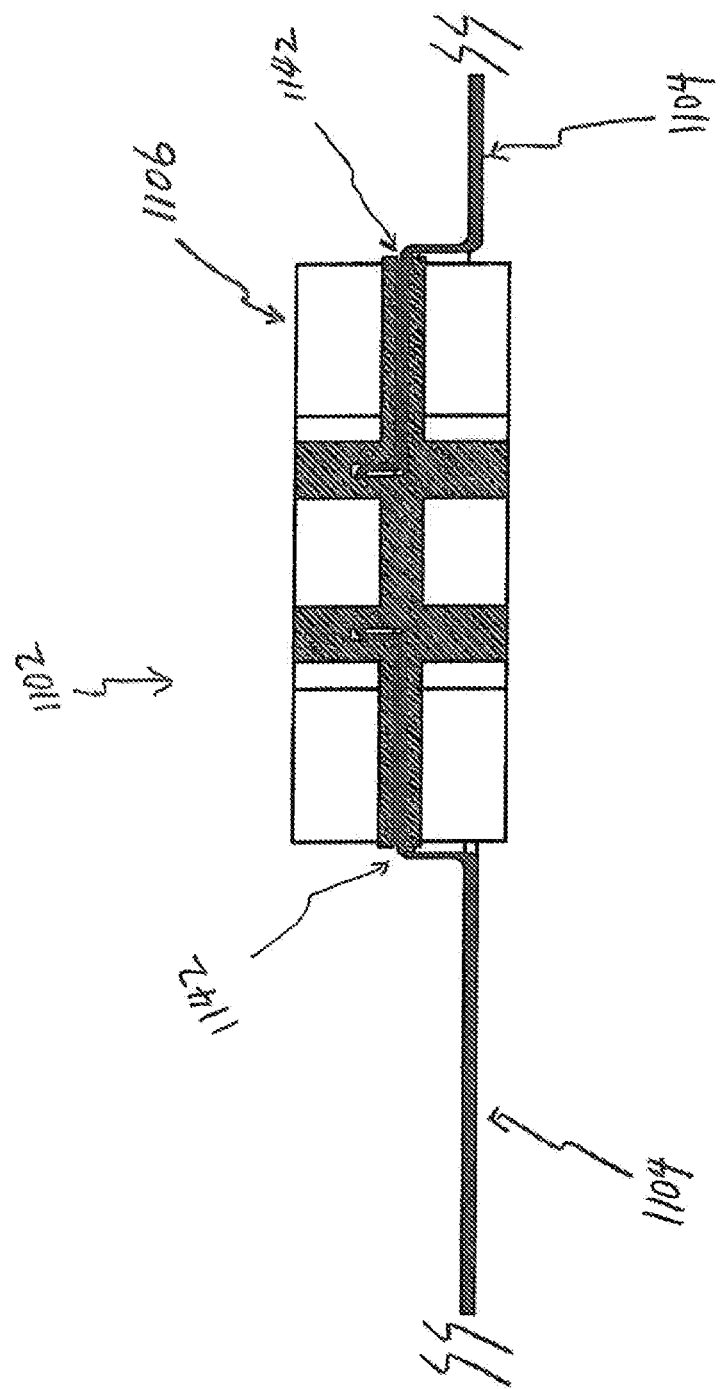
Figure 11G:
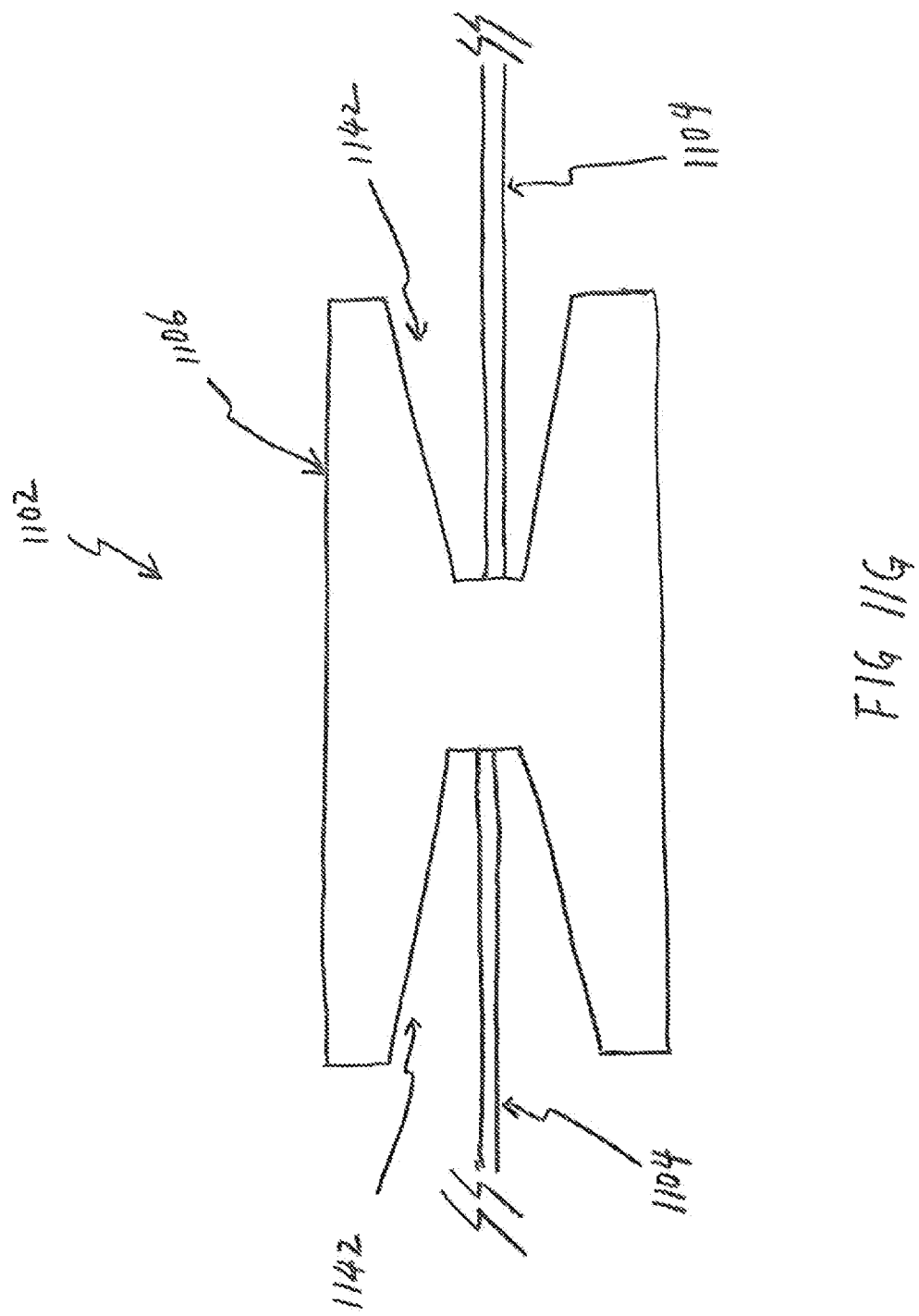
Figure 11H:
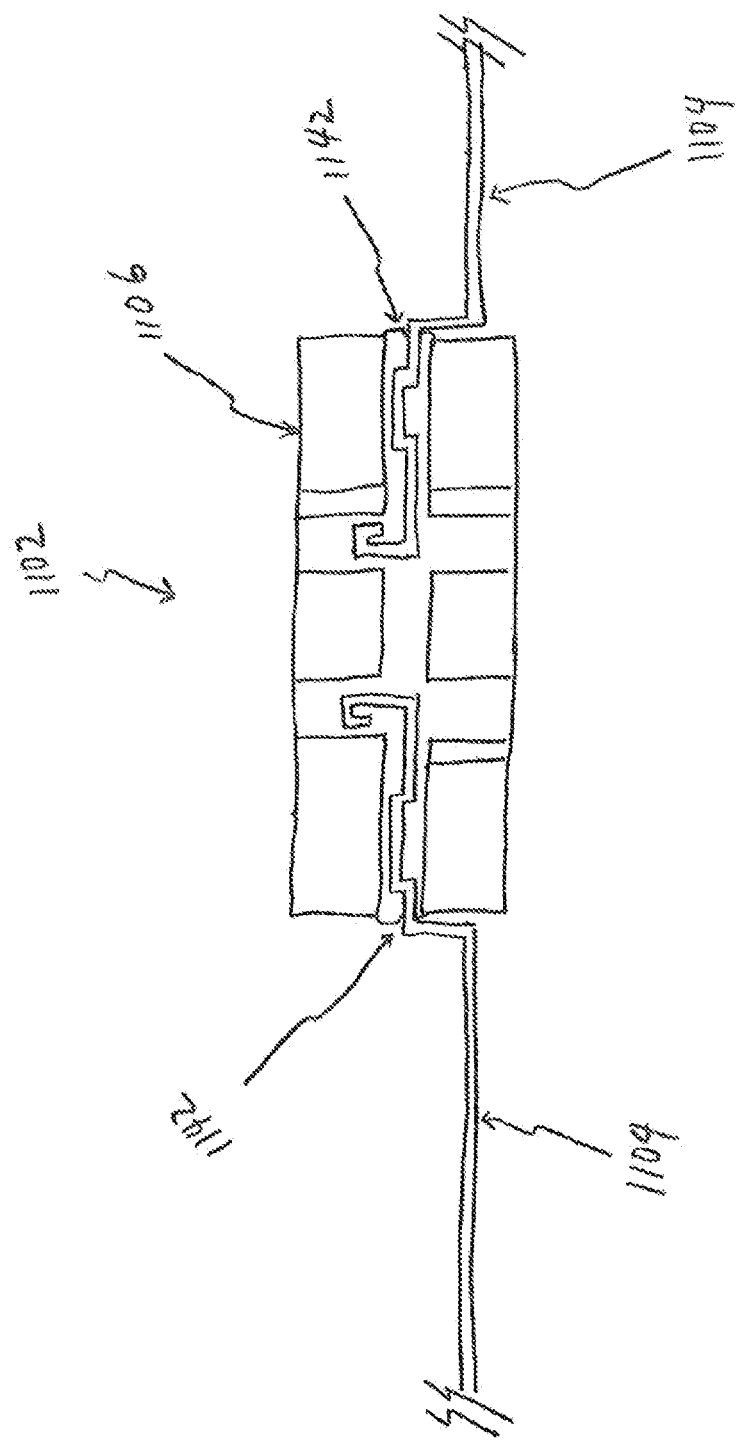

FIG. 11F illustrates how the drape (1104) may be incorporated with one or more drive transmission apparatuses (1106) for the sterile interface apparatus (1102) in accordance with one embodiment. FIG. 11F illustrates a cross sectional view of the drape (1104) and a drive apparatus (1106). As illustrates in FIG. 11F, the drape (1104) may be press fitted into a fluid seal channel (1142) of the drive transmission apparatus (1106). In some embodiments, the drive transmission apparatus (1106) may comprises of a first half and a second half and the two halves may be press fitted together with the drape disposed between the two halves. The channel (1142) may provide sufficient space or gap such that when the drive transmission apparatus (1106) is rotated or turned, the drape (1104) would not be grabbed (e.g., through friction) by the turning transmission apparatus (1106) and become twisted, tore, etc., for example. The channel (1142) may also provide a fluid tight seal or containment such that no fluid may leak through or pass the barrier (1102). In one embodiment, the fluid tight seal or containment may be a contact seal or contact type of seal. One example of a contact seal is illustrated in FIG. 11G. In another embodiment, the fluid tight seal or containment may be a labyrinth of grooves or channels on the surface of the fluid seal channel (1142) that would resist, minimize, or prevent fluid and/or particles from ingress and egress through the fluid seal channel (1142). In some embodiments, the fluid seal channel (1142) may be configured in a labyrinth or intricate pattern that would resist, minimize, or prevent fluid and/or particles from ingress and egress or pass through the fluid seal channel (1142) of the drive transmission apparatus (1106); one example is illustrated in FIG. 11H. In further embodiments, fluid tight seal or containment features may also be included in the drape (1104). In one example, the portion of the drape where it is mated with the drive transmission apparatus (1106) may include material or additional material that would facilitate forming contact seal with the channel (1142). The material or additional material may be additional drape material or it may be any suitable sealant material. In another example, the portion of the drape where it is mated with the drive transmission apparatus (1106) may include grooves or channels that would resist, minimize, or prevent fluid and/or particles from ingress and egress through the drape (1104) and drive transmission apparatus (1106) barrier. The grooves or channel that may be configured in various patterns. These grooves or channels on the drape (1104) may work independently or in combination with the fluid tight seal or containment features of the channel (1142) of the drive transmission apparatus (1106). For example, the grooves or channels on the drape (1104) may form matching, mating, interlocking, interlacing, or interweaving patterns.

The sterile drive interface apparatus may include one or more spline shafts. A flange may extend from or be connected to the spline shaft. The flange may have one or more tins, e.g., positioned on a bottom surface of the flange, and the fins may be separated by a gap. The sterile drive interface apparatus may further include a drape having a sterile surgical surface with one or more fins positioned thereon. The drape may have a shield positioned on the sterile surgical surface. The one or more fins on the drape may be positioned on the shield, and the fins may be separated by a gap. The shield may be configured to receive the spline shaft, e.g., the gaps between shield fins may be configured to receive flange fins and/or the gaps between flange fins may be configured to receive shield fins, such that the flange and/or spline shaft are rotatable relative to the shield and/or drape in a manner of reduced friction. A shield fin and flange fin may form a seal or barrier between the sterile operational environment and the non-sterile operational environment.

FIG. 12A illustrates one embodiment of a splayer assembly 1206 and a sterile drive interface apparatus 1202 configured to interface with the splayer assembly 1260 and an instrument driver. FIG. 12B illustrates the sterile drive interface apparatus 1202 coupled to the splayer assembly 1260 and an instrument driver 1261. The sterile drive interface apparatus 1202 forms a barrier between a sterile operational environment including the splayer assembly 1260 and a non-sterile operational environment including the instrument driver, and may transfer motion from the instrument driver to the splayer assembly 1260, e.g., without breaking the sterile barrier or without substantially or completely breaking the sterile barrier.

FIGS. 12C-12E illustrate top, bottom, and side perspective views of an embodiment of the sterile drive interface apparatus 1202, including a first spline shaft 1204, a flange 1208 extending from the first spline shaft, and a drape 1220 having one or more shields 1226 disposed between a stopper or portion of the first spline shaft 1214 and the flange 1208 or in embodiments utilizing more than one spline shaft (described below), between a second spline shaft and the flange 1208. The drape 1220 includes a sterile surgical surface 1222, a non-sterile working surface 1224, and a shield 1226 positioned on the sterile surgical surface 1222. The sterile drive interface apparatus may be sterile or substantially sterile on at least a portion of at least one side of the drape, e.g., the side facing the splayer assembly, instrument or instrument assembly and/or having a first spline shaft, flange, and/or shield.

In certain embodiments, the drape 1220 has one or more spline shafts or spline shaft assemblies inserted in the drape or connected or coupled to the drape and/or the shield on the drape, where the spline shafts or spline shaft assemblies are rotatable relative to the drape. A first spline shaft 1204 may extend through the drape 1220 or shield 1226 or from both sides of the drape such that a bottom portion of the first spline shaft 1204 may be operatively coupled to an instrument driver and a top portion of the first spline shaft 1204 may be operatively coupled to a splayer assembly 1260. A ring or stopper 1213 may attach to or extend from the first spline shaft 1204 or may contact the non-sterile working surface 1224 of the drape 1220 to reduce vertical movement to the first Spline shaft 1204. In other embodiments, a sterile drive interface apparatus 1202 may include a first spline shaft 1204 and a second spline shaft such that the first spline shaft 1204 may be operatively coupled to a splayer assembly 1260 and the second spline shaft may be operatively coupled to an instrument driver.

Figure 13B:
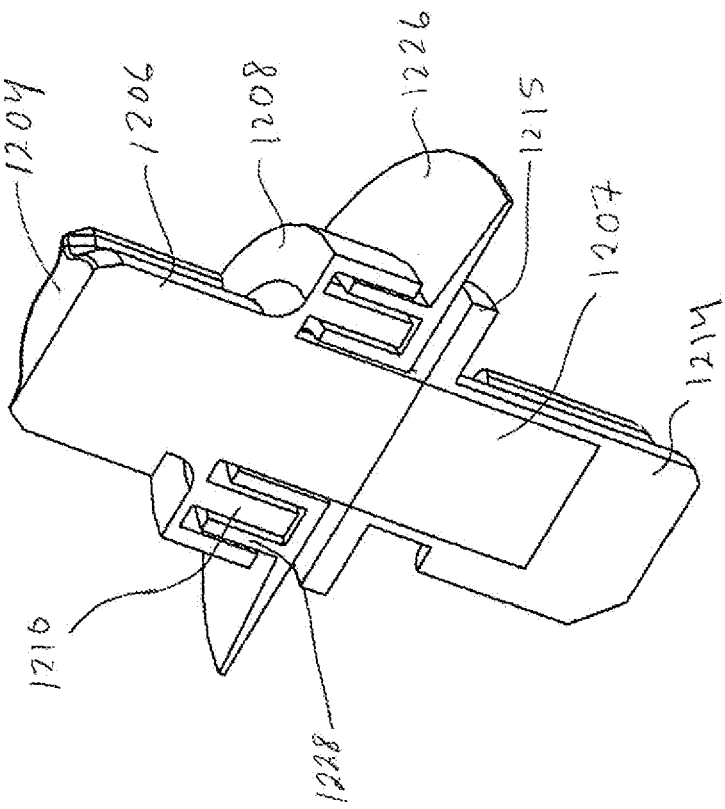
FIGS. 13A through 13D illustrate exemplary components of a sterile drive interface apparatus, with FIG. 13B illustrating a cross sectional view of those components.
Figure 13A:
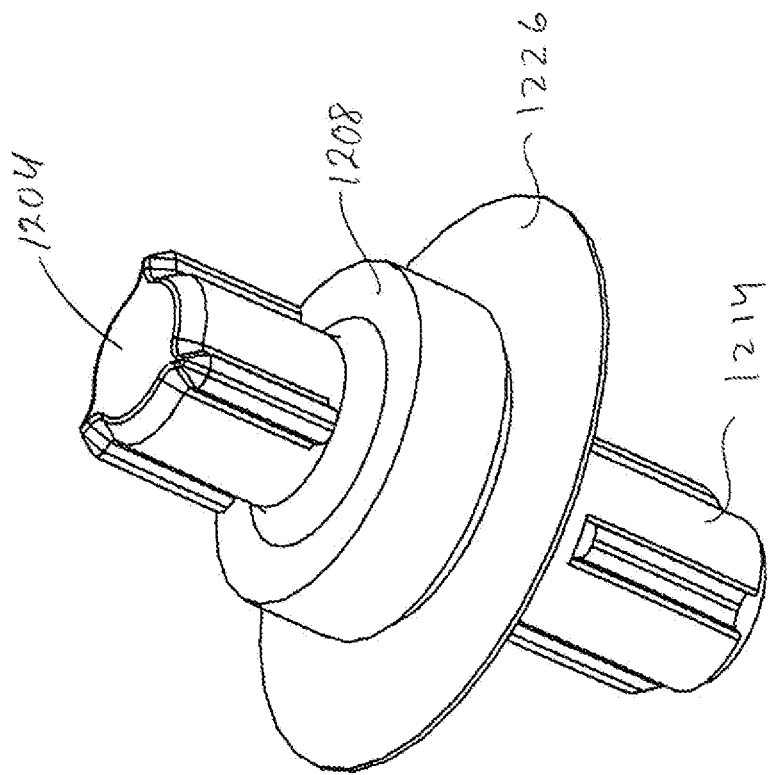
Figure 13D:
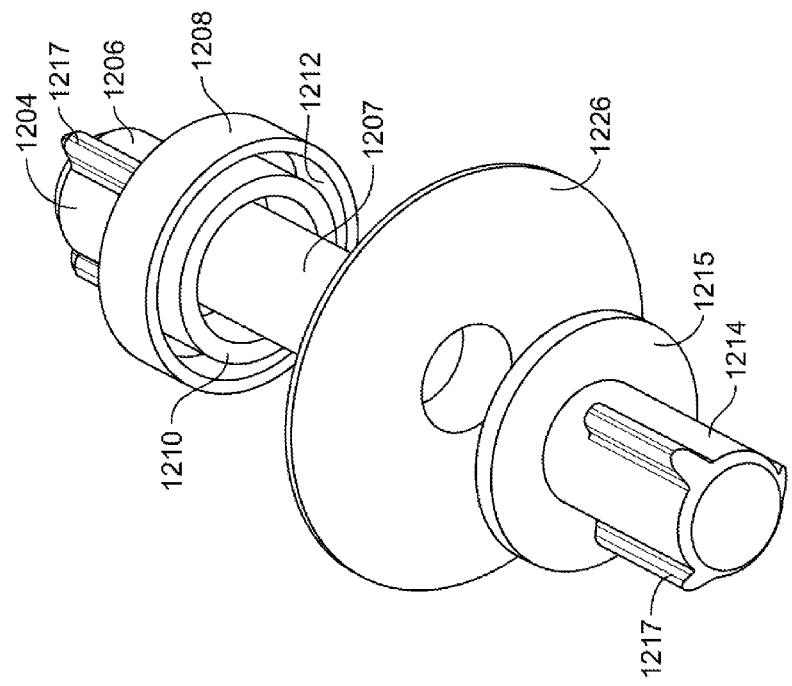

FIGS. 13A-13D illustrate the spline shafts, flange, and shield of one embodiment of a sterile drive interface apparatus with the drape not shown. The first spline shaft 1204 may include a first end portion 1206 and optionally a second end portion 1207. Flange 1208 may extend from or otherwise be connected to either or both of the first and/or second end portions 1206, 1207, in a direction substantially perpendicular to first spline shaft 1204. As shown in FIGS. 13B and 13D, flange 1208 has one or more fins 1210 on the flange, e.g., positioned on the bottom surface of the flange 1208. The fins 1210 may be separated by gaps 1212 such that a gap 1212 is situated between adjacent fins 1210. Optionally, fins may extend directly from a spline shaft in an embodiment with or without a flange.

The sterile drive interface apparatus 1202 may also include a second spline shaft 1214, which is configured or adapted to connect to the first spline shaft 1202. For example, the second spline shaft may be configured to receive the second end portion 1207 of the first spline shaft 1204 (as shown in the cross sectional view of FIG. 13B). The second spline shaft 1204 may include an opening such that the second end portion 1207 may be fastened or screwed into the second spline shaft 1214. Optionally, the second spline shaft 1214 and the first spline shaft 1204 may be attached through a variety of mechanisms, including but not limited to being press fit or friction fit together, screwed together where the opening and/or shaft are threaded, or attached using an adhesive or bonding mechanism. The second spline shaft 1214 may include a lip 1215 extending from a top portion of the second spline shaft 1214, which may contact the non-sterile working surface 1224 of the drape.

Figure 13C:
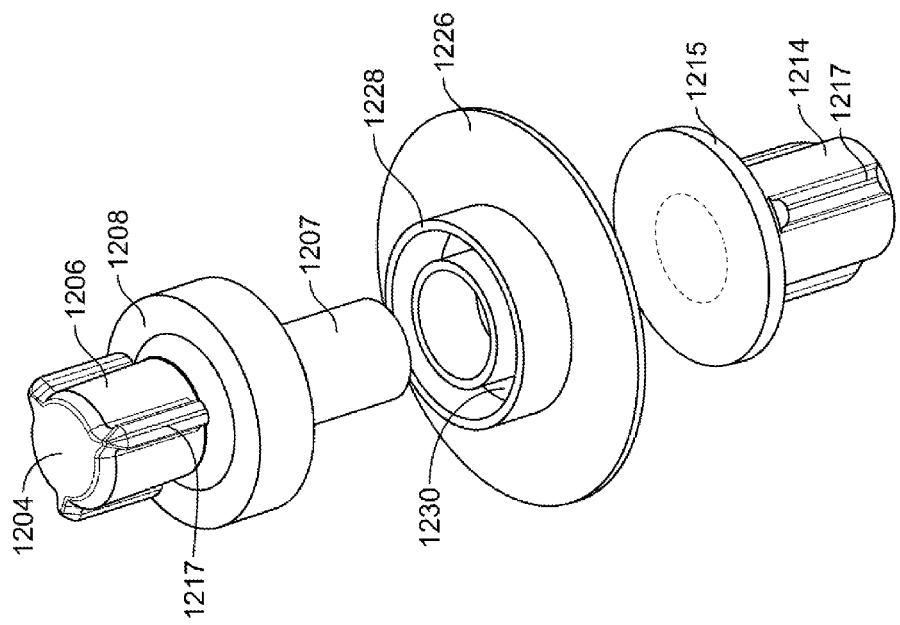

The shield 1226 of the drape (not shown) includes one or more fins 1228 extending from a top surface of the shield 1226 (as shown in FIGS. 13B and 13C). Optionally, fins may extend directly from the drape in certain embodiments. The fins 1228 may be separated by gaps 1230 such that a gap 1230 is situated between adjacent fins 1228. In certain embodiments, the gaps 1230 between the fins 1228 of the shield 1226 are configured to receive a fin 1210 of the flange 1208. For example, in certain embodiments the second end portion 1207 of the first spline shaft 1204 passes through an opening in the shield 1226 and through the drape, where the second end portion 1207 connects or attaches the second spline shaft 1214 to the first spline shaft 1204 and the gaps 1230 between the fins 1228 of the shield 1226 receive the fins 1210 of the flange 1208. The arrangement or connection of the drape and spline shafts could vary depending on the number of spline shafts and the particular design or configuration of the shield, flange, spline shaft and/or drape components. For example, a single spline shaft may be used where it is passed through the drape or shield and connects to a flange which will engage the drape or shield.

The gaps 1230 between the shield fins 1228 are configured to receive a flange fin 1210 such that a flange fin 1210, the flange 1208 and/or one or more spline shafts may rotate relative to the shield, shield fins 1228 and/or drape. The gaps 1230 between the shield fins 1228 may be configured to receive or engage a flange fin 1210 and/or the gaps between the flange fins 1210 may be configured to receive or engage a shield fin. The shield 1226 and/or drape 1220 are configured to receive a spline shaft where a flange fin 1208 may be positioned next to a shield fin 1228. This would be the case in an embodiment having one or more flange fins and/or one or more shield fins or a plurality of flange and shield fins.

The shield or drape is configured to receive one or more spline shafts and the shield fins and flange fins engage or interact such that the flange fins 1208, flange 1208 and/or one or more spline shafts may rotate relative to the shield, shield fins 1228 and/or drape in a manner of reduced friction or with a reduced frictional interaction; in a manner where frictional losses between the above components or between the instrument driver or RCM and the splayer assembly are minimized or reduced; in a manner where there is minimal, no or substantially no contact between the flange or spline shaft components and shield or drape components, e.g., such that there remains a gap or air gap between the fins; or in a frictionless or substantially frictionless manner, e.g., where any frictional losses do not hinder or interrupt the functionality or operation of a robotic surgical system or the sufficient transfer of motion from an instrument driver to a splayer assembly necessary to adequately operate a robotic surgical system for use on a patient.

When the sterile drive interface apparatus 1202 is in position or in use, the first spline shaft 1204 is coupled to the splayer assembly 1260 and the second spline shaft is coupled to the instrument driver, thereby minimizing or eliminating lateral or longitudinal movement or play of the flange 1208 and/or the first and/or second spline shafts 1204, 1214 relative to the shield 1226 and/or drape 1220. Thus, when the flange 1208 is in position on the shield 1226 and drape 1220, the flange 1208 and/or first and/or second spline shafts 1204, 1214 (which may be connected or adjoined) are substantially floating relative to the shield 1226 and/or drape 1220 and are rotatable relative to the shield 1226 and/or drape in a manner that minimizes, reduces or substantially eliminates friction or contact between the flange 1208 and/or first and/or second spline shafts 1204, 1214, and the shield 1226 and/or drape 1220, or between the shield fins 1228 and the flange fins 1208. The drape may include one or more shields and/or one or more spline shafts with flanges which are connected or coupled to the drape.

Also, the shield fins 1228 and flange fins 1210, alone or in combination, may form a seal, containment, or barrier between the sterile operational environment and the non-sterile operational environment. For example, the fins may interact to form a seal or barrier or containment that prevents or substantially prevents particles greater than about 1 mm in size from passing across the sterile drive interface apparatus and sterile barrier. Optionally, in certain embodiments, the seal or barrier or containment may prevent the passing of smaller particles or may provide a fluid tight seal.

The shield fins 1228 and/or the flange fins 1210 may have a variety of configurations or arrangements and when combined or engaged may create one or more channels which can form matching, mating, interlocking, interlacing, or interweaving patterns. The channels may form a labyrinth pattern or they may include a variety of configurations, shapes or patterns. The channels create an extended path through which fluid or particles must travel to pass from one side of the sterile barrier to the other, forming a seal, barrier or containment and thereby minimizing, reducing or eliminating penetration of or passing through the sterile barrier by fluid or particles. The channels may optionally provide a fluid barrier or fluid seal or fluid containment. In certain embodiments, the shield fins 1228 and/or the flange tins 1210 may be concentrically arranged and/or circular in shape. Optionally, the spline shafts and/or the drape may also help contribute to the barrier, containment or seal formed between the fins or form at least part of the channels.

In certain embodiments, the shield fins 1228 and/or flange fins 1210 may be coated with a hydrophobic coating. Any hydrophobic coating may be utilized, including but not limited to silicone, Parylene, and other materials or compounds having hydrophobic properties. The hydrophobic coating minimizes the ability of fluids to "wick" on the sterile drive interface apparatus, e.g., into the channels of the labyrinth, due to the change in surface tension that the coating provides, when compared to the native substrate material. The hydrophobic coating may provide a fluid tight seal or fluid resistant barrier between the sterile operational environment and the non-sterile operational environment by substantially preventing, resisting or eliminating fluid or particles from passing across the sterile drive interface apparatus and across the sterile barrier. The shield fins 1228 and/or flange fins 1210 alone or in combination with the hydrophobic coating may provide a fluid tight seal or fluid resistant barrier, or in other embodiments, a seal or barrier that is substantially fluid tight or fluid resistant allowing only a minimal amount of fluid passage.

Optionally, any portion of the flange or shield or the first or second spline shafts and/or drape may be coated with a hydrophobic coating. Materials used to manufacture the first or second spline shafts or the flange include but are not limited to polycarbonate, ultem, polysufone, PEEK, ABS, acetal, and various metals. Materials used to manufacture the shield or drape include but are not limited to polypropylene, pvc, polyurethane, and polyester. Also, in certain embodiments, a hydrophilic coating applied around the outside perimeter of the flange (or on other portions of the sterile drive interface apparatus, e.g., the drape, shield, or spline shafts) may provide a region that will attract fluids and keep them away from the channels or labyrinth channels of the fins to provide another mechanism or barrier for substantially preventing, resisting or eliminating fluid or particles from passing or leaking across the sterile drive interface apparatus. Optionally, a foam seal may be applied to the sterile drive interface apparatus that prevents fluid or particles from passing across the sterile barrier.

In certain embodiments described herein, the shield 1226 may be fastened or attached to the drape 1220 using a variety of mechanisms, which include but are not limited to heat bonding or affixing with adhesives. Optionally, one or more fins may extend directly from a drape where the drape is designed with or without shields. Optionally, the first spline shaft 1204 and/or flange 1208 may include an opening for receiving and attaching to a second spline shaft where the first spline shaft receives a first or second end of the second spline shaft. In other embodiments, the first or second spline shafts and flange may be attached using various fastening or attachment mechanisms known in the art.

In certain embodiments, the first and/or second spline shafts and other components of the sterile drive interface apparatus may include a variety of suitable designs or arrangements. For example, the first and second spline shafts may take on any suitable design or arrangement or configuration that allows the first and second spline shafts to connect or attach to one another. In certain embodiments, a first spline shaft may only have a first end portion and the second spline shaft may include a first end portion and a second end portion, where the first spline shaft receives or otherwise attaches to the second spline shaft. Optionally, a single spline shaft may be used which extends through the drape and/or shield and connects or fastens to a flange, rather than utilizing separate first and second spline shafts. In without a second spline shaft, an opposite ends of the first spline shaft are coupled to the instrument driver and splayer assembly. In certain embodiments, the flange may extend from or be connected to the single spline shaft, or where two shafts are used, the second spline shaft instead of the first spline shaft. In various embodiments, the spline shafts and flange can be constructed as a single spline shaft unit, combined units or as separate units. Any combination of these configurations is also contemplated, for example, the first and second spline shafts may be interchanged where either spline shaft can be positioned on the sterile or non-sterile side of the sterile interface apparatus or drape and may connect to either the splayer assembly or the driver interface. Also, either spline shaft may be connected to or include a flange. Optionally, the flange and/or shield may also be positioned on either side of the sterile interface apparatus.

FIG. 14A illustrates an exemplary splayer assembly 1260 having one or more spline pulleys 1264, which are rotatable within the splayer assembly 1260. The splayer assembly 1260 may be one component of an exemplary robotic surgical system.

FIG. 14B shows a robotic surgical system 1259 including the splayer assembly 1260 which may be coupled to an instrument. The splayer assembly may be coupled to an instrument driver 1261 via a sterile drive interface apparatus 1202 where the instrument driver 1261 is configured to manipulate the instrument in one or more degrees of motion via the sterile drive interface apparatus 1202 and the splayer assembly 1260.

FIG. 14C illustrates an exploded view of a spline pulley 1264 showing various components of the spline pulley 1264. The spline pulley 1264 includes a cage spline 1270, outer race 1272, pulley 1274, outer cage 1276, and cage 1278. A spline pulley may be positioned in a splayer assembly for receiving a spline shaft and/or in an instrument driver for receiving the opposite end of the spline shaft.

A splayer assembly may include any number of spline pulleys and a sterile drive interface apparatus may include any number of corresponding spline shafts depending on the particular use of the splayer assembly and robotic surgical system. In certain embodiments, a splayer assembly includes four spline pulleys and the sterile drive interface apparatus includes four spline shafts which engage the spline pulleys to transfer motion from the instrument driver to the splayer assembly and effect steering or articulating of the instrument. In other embodiments, the splayer assembly includes eight spline pulleys and the sterile drive interface apparatus includes eight spline shafts which engage the spline pulleys to transfer motion from the instrument driver to the splayer assembly and effect steering or articulating of the instrument.

Referring to FIGS. 14C and 14D, the spline pulley 1264 may have a plurality of spline teeth 1265 with spline receptacles 1266 formed between adjacent spline teeth 1265 configured to receive spline teeth 1217 positioned on the first and second portions of the spline shaft assembly or on the first and second spline shafts 1204, 1214.

Figure 15B:
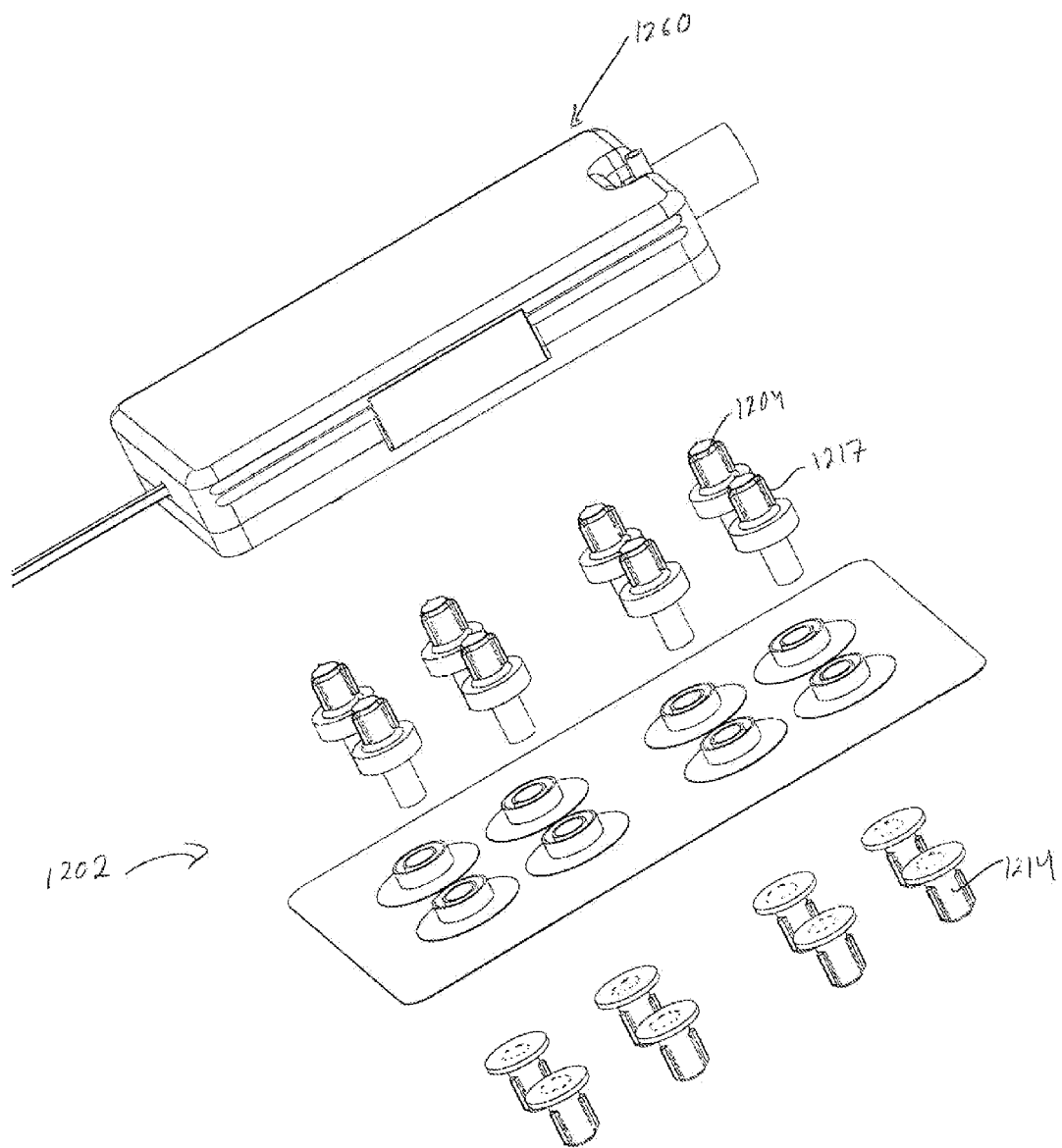

A sterile drive interface apparatus 1202, illustrated in FIG. 14B and in the exploded views of FIGS. 15A and 15B, is also provided. The sterile drive interface apparatus 1202 forms a sterile barrier between the splayer assembly 1260 and the instrument driver and may include a drape 1220 and a spline shaft assembly having one or more spline shafts and/or a flange, e.g., a first spline shaft 1204, second spline shaft 1214, and a flange. The spline shafts have one or more spline teeth 1217 positioned thereon. In certain embodiments, the male and female components of the spline shafts and spline pulley may be reversed where one or more spline pulleys include a male portion or shaft with spline teeth and one or both of the spline shaft ends may include receptacles for receiving the male portion or shaft and spline teeth of the spline pulley.

A bottom portion of the spline shaft assembly or a second spline shaft 1214 may be operatively coupled to the instrument driver and a top portion of the spline shaft assembly or a first spline shaft 1204 may be operatively coupled to the spline pulley 1264 in the splayer assembly 1260. Through this coupling, the sterile drive interface apparatus 1202 can transfer motion from the instrument driver to the splayer assembly 1262 without breaking or substantially disrupting the sterile barrier created by the sterile drive interface apparatus 1202.

Still referring to FIG. 15A or 15B, the spline pulleys 1264 have a greater number of receptacles 1266 than the number of spline teeth 1217 positioned on either the top or bottom portions of the spline shaft assembly or the first or second spline shafts. Also, the spline teeth 1265 forming the receptacles 1266 and/or the spline teeth 1217 positioned on the spline shafts may have chamfered ends. The chamfered ends and/or the arrangement of a greater number of spline pulley receptacles 1266 compared to the number of spline shaft teeth 1217 facilitate mating or meshing and/or disengagement between spline shafts and spline pulleys, where a reduced or minimal amount of insertion or pull out or coupling or decoupling force is required. For example, in certain embodiments, the force required to decouple a splayer assembly having 8 spline pulleys from the instrument driver or the RCM is from about 2 to 4 lbs or about 3 lbs.

The above designs also allow the spline shafts to mate or mesh with the spline pulleys substantially independent of the alignment of the spline shaft teeth relative to a spline pulley receptacle as a result of the larger number of receptacles relative to the spline shaft teeth and/or the chamfered ends that allow the teeth to slide into place even if misaligned.

The number of steps required to mate a spline shaft and a spline pulley are also reduced because the instrument driver or RCM is not required to rotate the attached spline shaft in order to locate a specific engagement position along the 360 degree diameter of a circular spline pulley for receiving the spline shaft, there being multiple engagement positions on any given spline pulley for receiving a spline shaft. The spline shafts and the spline pulleys may engage immediately upon installation without requiring substantial rotation or movement of the RCM, instrument driver, sterile drive interface apparatus, or splayer assembly relative to one another to locate an engagement or mating position.

In certain embodiments, the spline pulley comprises a plurality of receptacle arrangements and the spline shaft comprises a spline teeth arrangement where each of the receptacle arrangements are capable of receiving and mating with the spline teeth arrangement of the spline shaft, such that the spline shaft does not require substantial rotating or maneuvering in order to be received by or mate with, or prior to being received by or mating with the spline pulley. Indeed, multiple options or positions for mating between a spline shaft and spline pulley are provided. In certain embodiments, a single spline teeth arrangement is provided on a spline shaft and on or more of the receptacle arrangements or each of the receptacle arrangements in a spline pulley is capable of receiving the spline teeth arrangement proving multiple options for mating.

In certain embodiments, the spline pulley has 3 spline receptacles for every 1 spline tooth positioned on a spline shaft to facilitate mating and disengagement between the spline shaft and spline pulley. In certain embodiments, a spline pulley may have 9 spline receptacles and the corresponding spline shaft may have 3 spline teeth to facilitate mating and disengagement between the spline shaft and spline pulley. In certain embodiments, the splayer assembly is comprised of four spline pulleys and the sterile drive interface apparatus is comprised of four spline shafts which engage the spline pulleys to transfer motion from the instrument driver to the splayer assembly. In another embodiment, the splayer assembly is comprised of eight spline pulleys and the sterile drive interface apparatus is comprised of eight spline shafts which engage the spline pulleys to transfer motion from the instrument driver to the splayer assembly.

In certain embodiments, the number of spline pulley receptacles are equal to the number of spline shaft teeth. In certain embodiments, the robotic surgical system may be utilized in various surgical or catheter based procedures on a patient, for example, but not limited to, vascular procedures or procedures involving other parts of the patient.

In certain embodiments, a method of transmitting torque is provided. The method includes placing a sterile drive interface apparatus between an instrument driver and a splayer assembly. The sterile drive interface apparatus includes mating features configured to couple with mating features of the instrument driver and splayer assembly. The sterile drive interface apparatus is also configured to be disposed on a top surface of the instrument driver and a bottom surface of the splayer assembly. The sterile drive interface apparatus includes a spline shaft with a flange connected to the spline shaft and the flange having at least one fin positioned on the flange and a drape comprised of a sterile surgical surface and having at least one fin positioned thereon. The drape is configured to receive the first spline shaft such that the flange and spline shaft are rotatable relative to the drape in a manner of reduced friction and the drape fin and flange fin form a barrier between the sterile operational environment and the non-sterile operational environment. The sterile drive interface apparatus includes mating features configured to couple with mating features of the instrument driver and splayer assembly. The sterile drive interface apparatus creates a sterile barrier between a sterile operational environment and a non-sterile operational environment. The instrument driver is operated such that torque produced from the instrument driver is transmitted through the drive interface to the splayer assembly without breaking the sterile barrier. The sterile drive interface apparatus may be coated with a hydrophobic or a hydrophilic coating to provide a fluid tight seal between the sterile operational environment and the non-sterile operational environment.

Multiple embodiments and variations of the various aspects of the invention have been disclosed and described herein. Many combinations and permutations of the disclosed system are useful in minimally invasive medical intervention and diagnosis, and the system may be configured to support flexible robotics. One of ordinary skill in the art having the benefit of this disclosure would appreciate that the foregoing illustrated and described embodiments of the invention may be modified or altered, and it should be understood that the invention generally, as well as the specific embodiments described herein, are not limited to the particular forms or methods disclosed, but also cover all modifications, equivalents and alternatives. Further, the various features and aspects of the illustrated embodiments may be incorporated into other embodiments, even if no so described herein, as will be apparent to those ordinary skilled in the art having the benefit of this disclosure. Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A robotic surgical system, comprising:
   a splayer assembly coupled to an instrument, wherein the splayer assembly comprises a spline pulley rotatable within the splayer assembly, the spline pulley having a plurality of spline teeth with spline receptacles formed between adjacent spline teeth;
   a sterile drive interface apparatus forming a sterile barrier between the splayer assembly and an instrument driver, the sterile drive interface apparatus comprising a drape and a spline shaft assembly having spline teeth, wherein a bottom portion of the spline shaft assembly is operatively coupled to the instrument driver and a top portion of the spline shaft assembly is operatively coupled to the spline pulley positioned in the splayer assembly such that the sterile drive interface apparatus can transfer motion from the instrument driver to the splayer assembly;
   and wherein the spline pulley has more receptacles than the spline shaft assembly has spline teeth to facilitate mating between the spline shaft assembly and spline pulley.

2. The system claim 1, wherein the spline pulley comprises a plurality of receptacle arrangements and the spline shaft assembly comprises at least one spline teeth arrangement where the receptacle arrangements are capable of receiving and mating with the spline teeth arrangement of the spline shaft assembly without requiring that the spline shaft assembly be rotated prior to being received by a receptacle arrangement.

3. The system of claim 1, wherein the spline teeth forming the spline receptacles on the spline pulley and the spline teeth on the spline shaft assembly have chamfered ends to facilitate mating between the spline shaft assembly and the spline pulley in a manner that requires a minimal amount of insertion force.

4. The system of claim 1, wherein the sterile drive interface apparatus is adapted to transfer motion from the instrument driver to the splayer assembly without breaking the sterile barrier.

5. The system of claim 1, wherein the instrument is a steerable catheter.

6. The system of claim 1, wherein the spline pulley operates one or more control wires to manipulate the instrument in one or more degrees of motion.

7. The system of claim 1, wherein the spline pulley has 3 spline receptacles for every 1 spline tooth positioned on a spline shaft to facilitate mating between the spline shaft and spline pulley.

8. The system of claim 1, wherein the spline pulley has 9 spline receptacles and the spline shaft has 3 spline teeth to facilitate mating between the spline shaft and spline pulley.

9. The system of claim 1, wherein the splayer assembly is comprised of four spline pulleys and the sterile drive interface apparatus is comprised four spline shafts which engage the spline pulleys to transfer motion from the instrument driver to the splayer assembly.

10. The system of claim 1, wherein the splayer assembly is comprised of eight spline pulleys and the sterile drive interface apparatus is comprised of eight spline shafts which engage the spline pulleys to transfer motion from the instrument driver to the splayer assembly.

11. A robotic surgical system, comprising:
a splayer assembly coupled to an instrument, wherein the splayer assembly comprises a spline pulley rotatable within the splayer assembly;
a sterile drive interface apparatus forming a sterile barrier between the splayer assembly and an instrument driver, the sterile drive interface apparatus comprising a first spline shaft; a flange extending from the first spline shaft and having at least two fins positioned on a bottom surface of the flange the at least two fins being separated by a gap; a second spline shaft connected to the first spline shaft; and a drape disposed between the second spline shaft and the flange of the first spline shaft, the drape comprised of a sterile surgical surface and a shield positioned on the sterile surgical surface the shield having at least two fins extending therefrom which are separated by a gap;
wherein the gap between the fins of the shield is configured to receive one of the fins of the flange and the gap between the fins of the flange are configured to receive one of the fins of the shield, such that the flange and first and second spline shafts are rotatable relative to the shield; and
wherein the second spline shaft is operatively coupled to the instrument driver and the first spline shaft is operatively coupled to the spline pulley positioned in the splayer assembly such that the sterile drive interface apparatus can transfer motion from the instrument driver to the splayer assembly without breaking the sterile barrier.

12. The system of claim 11, wherein a number of mating elements located on the spline pulley is greater than a number of mating elements located on the spline shaft to facilitate mating between the spline shaft and spline pulley.

13. A robotic surgical system, comprising:
a splayer assembly coupled to an instrument, wherein the splayer assembly comprises a spline pulley rotatable within the splayer assembly the spline pulley having at least one first mating element; and
a sterile drive interface apparatus forming a sterile barrier between the splayer assembly and an instrument driver, the sterile drive interface apparatus comprising a drape and a spline shaft assembly having at least one second mating element, wherein the drape comprises a sterile surgical surface having at least one drape fin positioned thereon and wherein the spline shaft assembly comprising a first spline shaft that includes a flange having at least one flange fin positioned on the flange, wherein at least one of the drape fin and the flange fin are coated with a hydrophobic coating wherein a bottom portion of the spline shaft assembly is operatively coupled to the instrument driver and a top portion of the spline shaft assembly is operatively coupled to the spline pulley positioned in the splayer assembly such that the sterile drive interface apparatus can transfer motion from the instrument driver to the splayer assembly and wherein the flange fin and the drape fin cooperate to form a fluid tight seal between the sterile operational environment and the non-sterile operational environment and wherein the flange fin and the drape fin are arranged in a concentric manner when the first spline shaft is coupled to the drape so as to create a channel configured in a labyrinth pattern to provide a seal between the sterile operational environment and the non-sterile operational environment.

14. The system of claim 13, wherein a number of first mating elements on the spline pulley is greater than a number of second mating elements on the spline shaft to facilitate mating between the spline shaft and spline pulley.

15. The system of claim 13, wherein the spline pulley comprises a plurality of first mating dements in the form of receptacles and the spline shaft comprises a plurality of second mating elements in the form of spline teeth where the receptacles are capable of receiving and mating with the spline teeth of the spline shaft without requiring that the spline shaft be rotated prior to being received by the spline pulley.

16. The system of claim 15, wherein spline teeth forming the receptacles on the spline pulley and the spline teeth on the spline shaft assembly have chamfered ends to facilitate mating between the spline shaft assembly and the spline pulley in a manner that requires a minimal amount of insertion force.

17. The system of claim 15, wherein the spline pulley has 3 receptacles for every 1 spline tooth positioned on a spline shaft to facilitate mating between the spline shaft and spline pulley.

18. The system of claim 15, wherein the spline pulley has 9 receptacles and the spline shaft has 3 spline teeth to facilitate mating between the spline shaft and spline pulley.

19. The system of claim 13, wherein the splayer assembly is comprised of four spline pulleys and the sterile drive interface apparatus is comprised of four spline shafts which engage the spline pulleys to transfer motion from the instrument driver to the splayer assembly.

20. The system of claim 13, wherein the splayer assembly is comprised of eight spline pulleys and the sterile drive interface apparatus is comprised of eight spline shafts which engage the spline pulleys to transfer motion from the instrument driver to the splayer assembly.

21. The system of claim 13, wherein the sterile drive interface apparatus is configured to transfer motion from an instrument driver to a splayer assembly without breaking the sterile barrier.

22. The system of claim 13, wherein the instrument is a steerable catheter.

23. The system of claim 13, wherein the spline pulley operates one or more control wires to manipulate the instrument in one or more degrees of motion.

24. A robotic surgical system, comprising:
- a splayer assembly coupled to an instrument, wherein the splayer assembly comprises a spline pulley rotatable within the splayer assembly the spline pulley having at least one first mating element; and
- a sterile drive interface apparatus forming a sterile barrier between the splayer assembly and an instrument driver, the sterile drive interface apparatus comprising a drape and a spline shaft assembly having at least one second mating element, wherein the drape comprises a sterile surgical surface having at least one drape fin positioned thereon and wherein the spline shaft assembly comprising a first spline shaft that includes a flange having at least one flange fin positioned on the flange, wherein a bottom portion of the spline shaft assembly is operatively coupled to the instrument driver and a top portion of the spline shaft assembly is operatively coupled to the spline pulley positioned in the splayer assembly such that the sterile drive interface apparatus can transfer motion from the instrument driver to the splayer assembly and wherein the flange fin and the drape fin are arranged in a concentric manner when the first spline shaft is coupled to the drape so as to create a channel configured in a labyrinth pattern to provide a seal between the sterile operational environment and the non-sterile operational environment.

* * * * *